United States Patent [19]
Melchers et al.

[11] Patent Number: 5,993,808
[45] Date of Patent: *Nov. 30, 1999

[54] CHITINASE, DNA CODING THEREFOR AND PLANTS CONTAINING SAME

[75] Inventors: Leo Sjoerd Melchers, Leiden; Marion Apotheker-De Groot, Haarlem; John Ferdinand Bol, Oegstgeest; Bernardus Johannes Clemens Cornelissen, Warmond; Hubertus Josephus Maria Linthorst; Anne Silene Ponstein, both of Leiden; Marianne Beatrix Sela-Buurlage, Amersfoort, all of Netherlands

[73] Assignees: Mogen International NV; Rijksuniversiteit Te Leiden, both of Leiden

[21] Appl. No.: 08/591,629

[22] PCT Filed: Aug. 17, 1994

[86] PCT No.: PCT/EP94/02761

§ 371 Date: Feb. 15, 1996

§ 102(e) Date: Feb. 15, 1996

[87] PCT Pub. No.: WO95/05467

PCT Pub. Date: Feb. 23, 1995

[30] Foreign Application Priority Data

Aug. 17, 1993 [EP] European Pat. Off. .............. 93202425

[51] Int. Cl.⁶ ............................. A61K 38/47; C12N 9/24; C12N 9/42
[52] U.S. Cl. ........................ 424/94.61; 435/200; 435/209
[58] Field of Search ................................... 435/209, 200; 424/94.61

[56] References Cited

FOREIGN PATENT DOCUMENTS

| | | |
|---|---|---|
| 0440304 | 8/1991 | European Pat. Off. . |
| 0531218 | 3/1993 | European Pat. Off. . |
| 4117026 | 11/1992 | Germany . |

OTHER PUBLICATIONS

C.G. Bae et al. "Purification and Characterization of Two Acidic Chitinases Having and Lacking N–Terminal Cysteine–Rich Domain From Root of Rice (Oryza sativa L.)", Mol. Cells 3(3), 1993.

A. Elghaouth et al., "Glucanohydrolases and Inhibitory Activity to Botrytis–cinerea in Extracts From Strawberry Fruits", Can. J. Plant Pathology 13(4): 315–320, Dec. 1991.

E. Delcampillo et al. "Identification and Kinetics of Accumulation of Proteins Induced by Ethylene in Bean Abscission Zones", Plant Pathology 98(3): 955–961, Mar. 1992.

Fritig, B. et al. "Virus Induced Glycanhydrolases . . . " NATO ASI Series, vol. H.36, Signal Molecules in Plants & Plant–Microbe Interactions, Springer–Verlag Berlin, Heidelberg 1989.

Melchers, L.S. "A new class of tobacco . . . ".

van Huijsduijenen, R.A.M. et al. "cDNA cloning of six . . . " EMBO Journal, vol. 5, No. 9, pp. 2057–2061, 1986.

Schuler, et al *Proteins: Structure, Function and Genetics* 9 180–190 (1991) A Workbench for Multiple Alignment Construction and Analysis.

van Loon, et al, *Plant Molecular Biology Reporter* 12 (3) 245–264 (1994) Genetic Resources: Recommendations for Naming Plant Pathogenesis–Related Proteins.

Bol, J.F. "Structure and Expression of Plant . . . " Chapter 11, pp. 201–221.

Heitz, T. et al. "Molecular Characterization . . . " Mol. Gen. Genet (1994) Springer Verlag 1994.

*Primary Examiner*—Rebecca E. Prouty
*Attorney, Agent, or Firm*—Ladas & Parry

[57] ABSTRACT

There is provided a method for inhibiting growth and/or germination of a fungus, by contacting the fungus, or causing the fungus to be contacted with a composition including an effective amount of a pathogenesis-related protein occurring naturally in a plant. The protein has endochitinase activity, antifungal activity and a molecular weight of about 40 to 43 kDa as judged by Sodium Dodecyl Sulphate Polyacrylamide electrophoresis. There is also provided a composition for inhibiting growth and/or germination of a fungus. The composition includes a pathogenesis-related protein occurring naturally in a plant. The protein has endochitinase activity, antifungal activity and a molecular weight of about 40 to 43 kDa as judged by Sodium Dodecyl Sulphate Polyacrylamide electrophoresis. The composition also includes β-1,3-glucanase in an amount sufficient to enhance the effectiveness of the composition in inhibiting the growth or germination of the fungus.

15 Claims, 10 Drawing Sheets

CHITINASE, DNA CODING THEREFOR AND PLANTS CONTAINING SAME

FIELD OF THE INVENTION

The present invention relates to chitinases from plant origin, DNA coding therefor, and plants which have been transformed to contain and express said recombinant polynucleotides to produce or overproduce said chitinase. The invention further provides methods to protect plants from pathogen attack, as well as plants obtainable thereby. The invention further comprises antipathogenic compositions containing as active ingredient a chitinase according to the invention.

STATE OF THE ART

Plants react to stresses such as attack by pathogens, chemical treatment and wounding, by accumulating a large number of proteins. One of the best studied plant responses is the induced expression of so-called pathogenesis-related proteins, PR-proteins, (Bowles, D. 1990, Annu. Rev. Biochem. 59, 873–907); Linthorst, H. J. M., 1991, Crit. Rev. Plant Sci. 10, 123–150).

PR-proteins can be classified into at least five families (PR-1 to PR-5) based on structure and/or activity. In tobacco, within each family of PR-proteins both intracellular (class-I) and extracellular (Class-II) isoforms are distinguished.

Among the PR-proteins are chitinases, which constitute the PR-3 family (Legrand M., et al, 1987, Proc. Natl. Acad. Sci. USA, 84, 6750–6754). The class-I chitinases possess antifungal activity (Broekaert W. F. et al, 1988, Physiol. Mol. Plant Pathol. 33, 319–331), especially in combination with β-1,3-glucanase (Schlumbaum A. et al, 1986, Nature 324, 365–367), classified as the PR-2 family (Kauffmann S. et al, 1987, EMBO J. 6, 3209–3212).

The occurrence of chitinases and the cloning of their corresponding cDNAs has been described for a large number of plant species, both dicotyledonous and monocotyledonous species (for a recent review, vide Collinge D. B. et al, 1993, The Plant Journal 3(1), 31–40). Chitinases are classified according to their primary structure into three classes (Shinshi H. et al, 1990, Plant Mol. Biol. 14, 357–368). Recently chitinases have been found that do not fit into this classification: these chitinases have been proposed to form class-IV. The class I chitinases are characterised by the presence of an approximately 40 amino acid cysteine rich domain.

The class-II chitinases resemble the class-I chitinases, inter alia by their amino acid sequence homology, but the former lack a cystein-rich domain.

The class-III chitinases do not share sequence similarity with chitinases of either of the classes I or II. The class-IV chitinases, as proposed by Collinge et al. supra, comprise sugar beet chitinase IV (Mikkelsen J. D. et al, 1992, In *Advances in Chitin and Chitosan* (Brine, C. J. Sandford, P. A. and Zikakis, J. P. eds. Amsterdam Elsevier, in press) and the basic rape chitinase ChB4 (Rasmussen U. et al, 1992, Planta, 187, 328–334), as well as the acidic bean PR4 chitinase (Margis-Pinheiro M. et al, 1991, Plant. Mol. Biol. 17, 247–253), show sequence similarity with the class I chitinases, contain a N-terminal cystein-rich domain, but are smaller than the class-I chitinases due to a number of deletions. The molecular weights of plant chitinases range on average from about 26 to about 36 kDa.

By cloning the genes coding for PR-proteins, altering their expression patterns by placing the genes under the control of non-natural, e.g. consitutive, regulatory elements, and reintroducing those constructs in plants, it is possible to reduce the susceptibility of plants to pathogen-attack, in particular fungal attack (European patent application 0 440 304 A1; EP 0 460 753). Simultaneous expression in transgenic plants of class-I chitinases and β-1,3-glucanases produces a marked enhancement of fungal resistance in transgenic plants, showing the value of combining antipathogenic proteins.

There is a continuous need for the identification of new chitinases for use in antifungal compositions and/or for the cloning of cDNAs or genes encoding such chitinases, to study the effect of expressing these cDNAs or genes in transgenic plants and evaluate the susceptibility of said plants to pathogenic attack, in particular to fungal attack.

It is an object of the present invention to provide novel antipathogenic proteins, DNA coding therefor, as well as plants which contain and express such DNA, to impart on such plants a reduced susceptibility to pathogen attack, in particular fungal attack.

SUMMARY OF THE INVENTION

The present invention provides a protein free from other plant proteins which has endo-chitinase activity, antifungal activity and a molecular weight of about 40 to 43 kDa as judged by Sodium Dodecyl Sulphate Polyacrylamide electrophoresis. A more preferred protein is one which is obtainable from leaves of TMV-induced tobacco plants. A still more preferred protein is one having an amino acid sequence as represented in SEQIDNO: 2 or 8, or a fragment thereof having chitinase activity. Also provided are proteins according to the invention wherein one or more amino acids are substituted, deleted, or added without abolishing chitinase activity.

Another embodiment of the invention is an antifungal composition comprising as active ingredient a protein according to the invention. A preferred composition is one which comprises in addition to said protein a further protein acting synergistically with the said protein on fungi. Further preferred compositions comprise a β-1,3-glucanase, preferably a basic β-1,3,-glucanase and/or a chitinase, preferably a class I chitinase, more preferably from tobacco.

A further embodiment of the invention is an isolated DNA sequence which comprises an open reading frame encoding a protein according to the invention, preferably one having the sequence as represented in SEQIDNO: 2 or SEQIDNO: 8, or DNA sequences hybridizing therewith under stringent conditions.

The invention also comprises a plant expressible recombinant DNA sequence which comprises a DNA sequence encoding a protein according to the invention, or a precursor of said protein, said DNA sequence being physically linked to regulatory elements necessary for expression of said DNA sequence in plants to produce said protein. A preferred plant expressible recombinant DNA sequence is one, wherein said DNA sequence encodes a protein precursor having the amino acid sequence represented by SEQIDNO: 2 or SEQIDNO: 8. Another preferred plant expressible recombinant DNA sequence comprises the DNA sequence as represented in SEQIDNO: 1 or 7.

The invention also encompasses a cloning vehicle or a vector containing a DNA sequence according to the invention, as well as bacterial strains containing such a cloning vehicle or vector. Also provided are bacterial strains of the genus Agrobacterium containing a vector suitable for transferring DNA according to the invention to plant cells and plants.

Other embodiments of the invention comprise plant genomes, plant cells comprising such genomes and plants regenerated from such plant cells, which as a result thereof produce or overproduce proteins according to the invention. Ideally, expression of DNA encoding proteins according to the invention is optimised to render plants less susceptible to pathogen attack, in particular fungal attack.

The invention further comprises plant material such as a bulb, flower, fruit, leaf, pollen, root or root culture, seed, stalk, tubers or microtubers, and the like, comprising one or more cells which have incorporated therein plant expressible DNA according to the invention.

The invention also provides a method for breeding a plant variety which has reduced susceptibility to fungi, characterized in that at least one of the parental lines has a recombinant DNA genome according to the invention, as well as a method for reducing the damage to plants under cultivating conditions. Further aspects of the invention, various ways to practice the invention and some advantages are outlined in the detailed description.

The invention is illustrated by the following Figures.

DESCRIPTION OF THE FIGURES

FIGS. 1A–1C. Nucleotide sequence of the Cluster-A gene and a homologous cDNA clone. The complete nucleotide and amino acid sequence of the genomic cluster-A clone are shown in line b and line c, respectively. Above the nucleotide sequence only the nucleotides which are different in the cDNA clone are indicated in line a. Similarly, below the Cluster-A protein sequence only the amino acids which are different in the cDNA sequence are indicated in line d. The amino acid sequence determined by sequencing the protein are underlined. The putative cleavage site of the signal peptide, between residues (Ser (S) and Gln (Q), is indicated by an arrow.

DETAILED DESCRIPTION OF THE INVENTION

Figure 2:
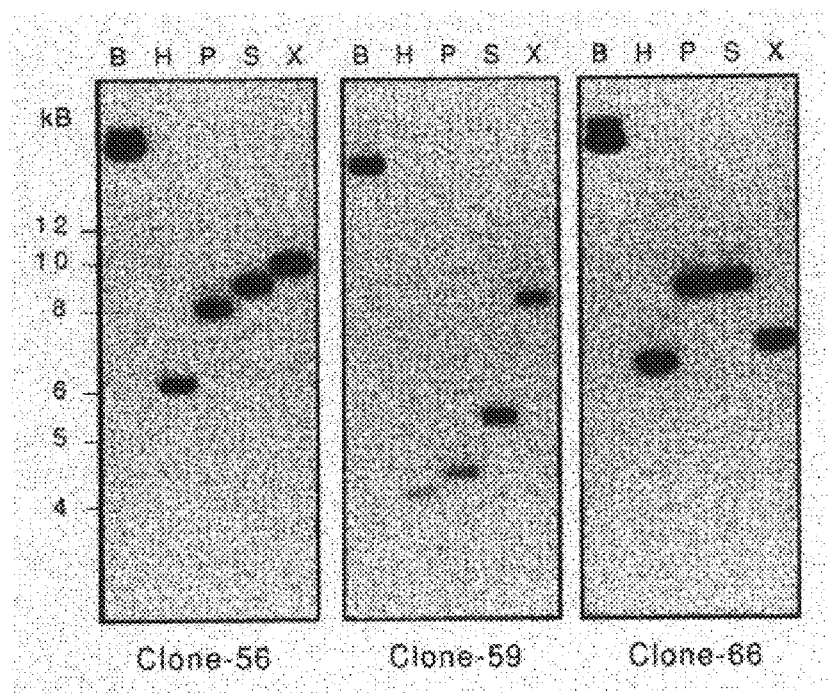
FIG. 2. Southern blot analysis of three clones containing sequences homologous to the tobacco Cluster-A gene. Three genomic clones of tobacco (clone-56; 59; 66) were purified and digested with either BamHI, HindIII, PstI, SstI or XbaI, lanes 1 to 5 respectively, and electrophoresed on an 0.8% agarose gel. The gel was blotted and hybridized with the cluster-A cDNA and washed at 65° C. in 0.1× SSPE, 0.1% SDS.

The present invention provides a novel class of chitinases which can be isolated from plants. The invention provides in particular an approximately 40–43 kDa protein from TMV-induced tobacco leaves. This protein was found to be encoded by an open reading frame which closely resembles a cDNA previously called cluster-A (Hooft van Huijsduijnen et al (Hooft van Huijsduijnen R. A. M. et al, The EMBO Journal 5(9), 2057–2061). In this reference 6 clusters (A to F) of mRNAs have been described which are TMV- and salicylate-inducible in tobacco. The authors characterized the mRNAs of the six clusters by hybrid-selected in vitro translation. The translation products of the hybrid-selected mRNA corresponding to the largest cluster-A cDNA clone produced a complex pattern of proteins of 40, 35, 31, 28 and 25 kDa respectively (See lane 6, FIG. 3 of Hooft van Huijsduijnen et al, supra). The protein actually produced by this cDNA sequence was never determined. None of the protein fragments was ever purified, nor was the structure of either of these fragments determined. No physiological activity was known for any of these protein fragments either.

According to the present invention the protein corresponding with this Cluster-A cDNA was purified to homogeneity from TMV-induced tobacco leaves using an antiserum. The antiserum was raised against a purified protein produced in *E. coli* transformed with a cDNA clone from tobacco hybridising with PROB40. The clone PROB40 was known to cross-hybridise with Cluster-A cDNA, (Hooft van Huijsduinen et al, (supra).

Figure 1A:
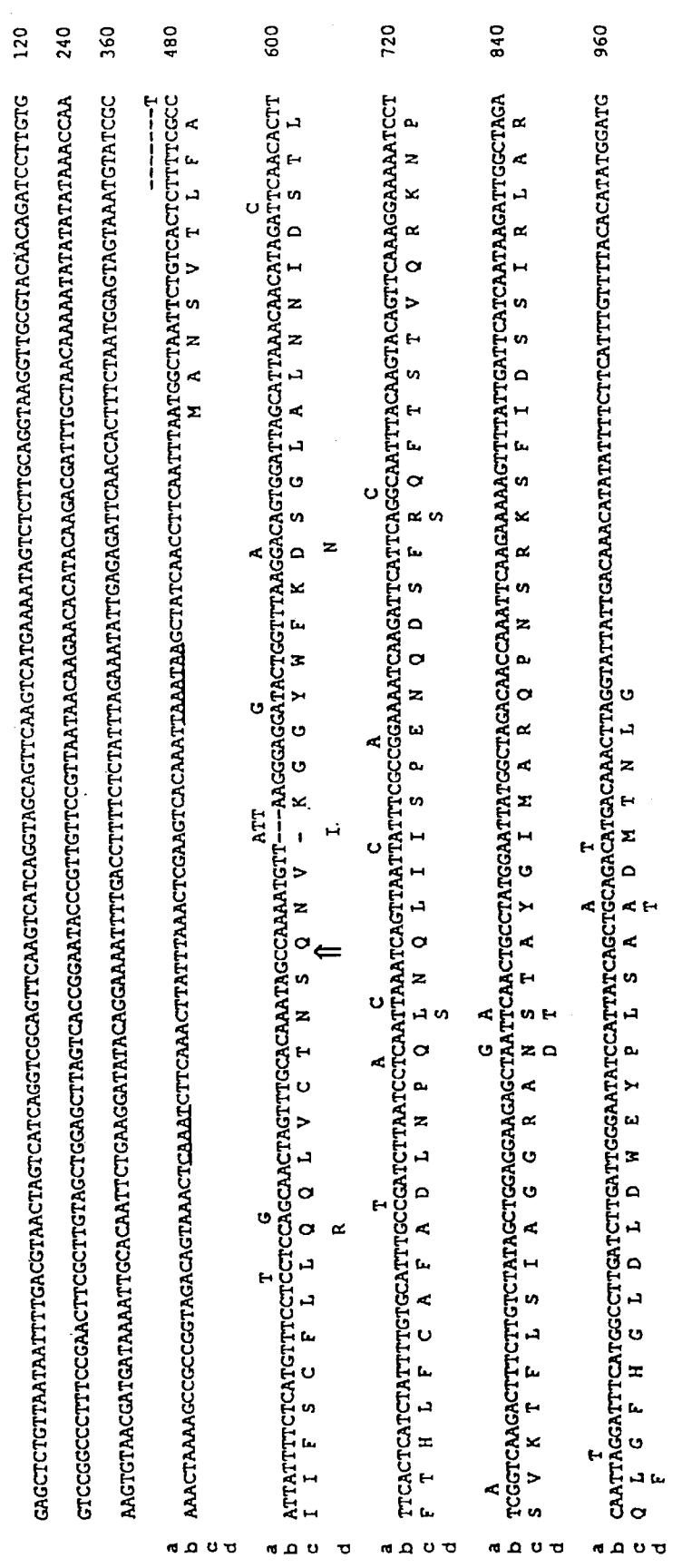
Figure 1B:
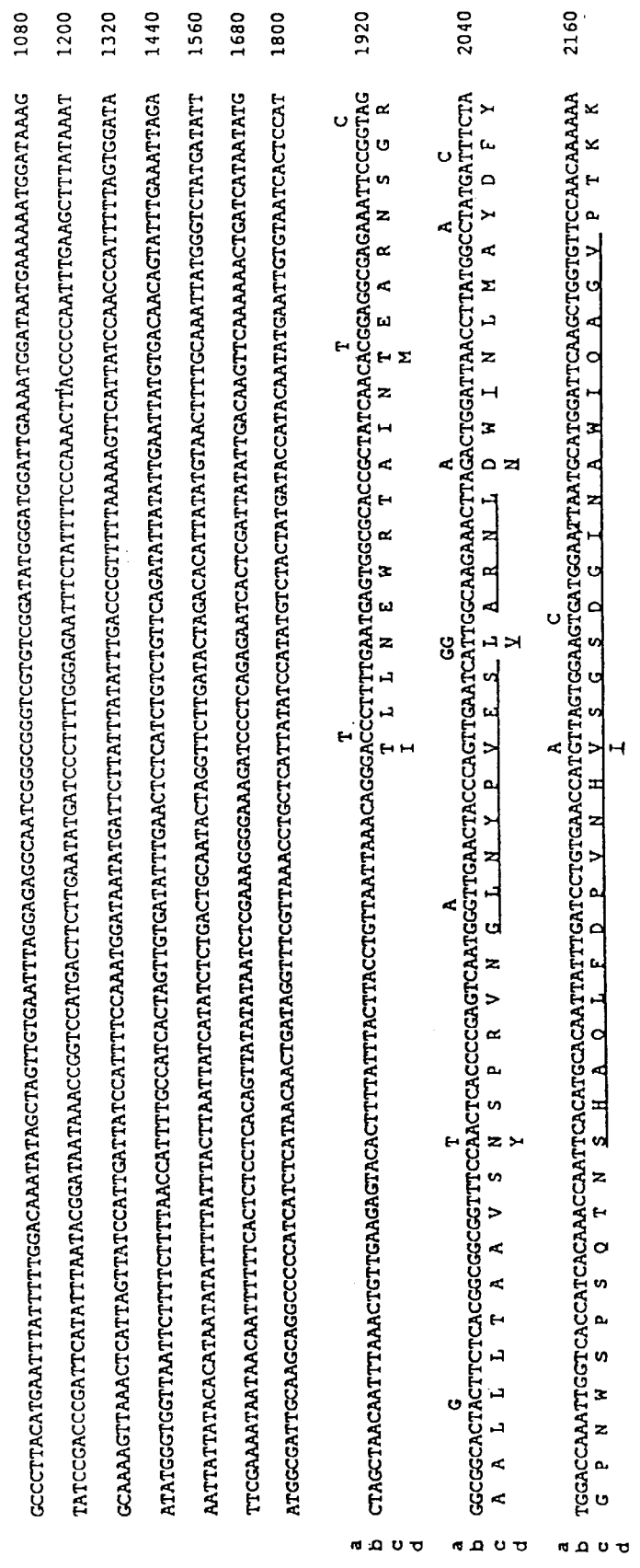
Figure 1C:
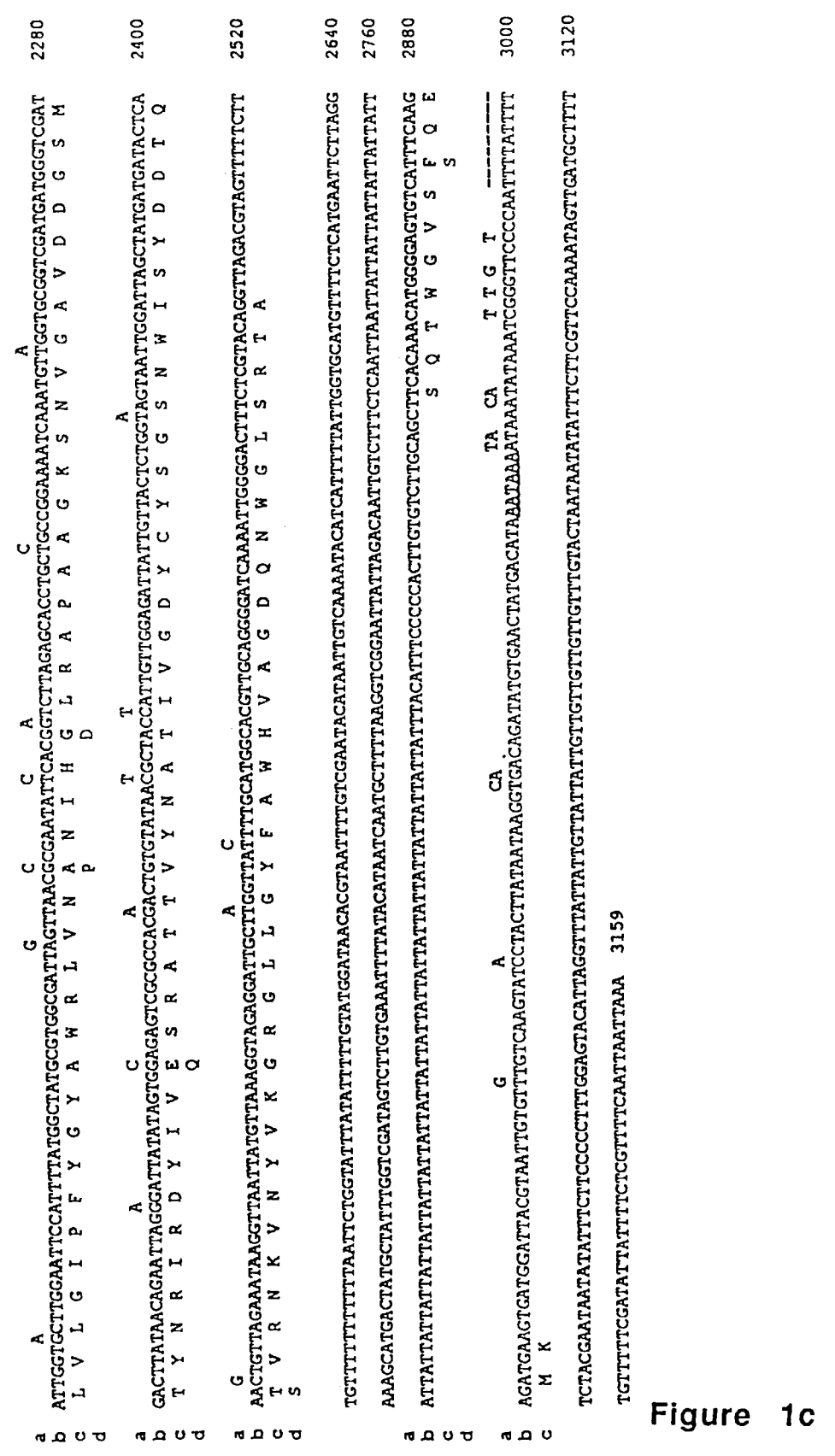

Using this antiserum in the identification and purification process, Cluster-A protein could be isolated from TMV-infected tobacco leaves in sufficient quantity to study its physiological and antipathogenic activity. A partial amino acid sequence of the isolated protein was obtained from sequencing the purified protein from tobacco; it was almost identical with the amino acid sequence deduced from the cDNA (FIG. 1).

The Cluster-A protein was found to possess low chitinase activity on tritiated chitin as a substrate, about 250–500 times lower than the class I chitinases from tobacco. However, when tested with a colorimetric assay on a soluble chitin substrate, its activity was found to be about two fold higher than the class I chitinases. No exochitinase activity or lysozyme activity could be detected. Altogether, it was concluded that the Cluster-A represented an endochitinase, but with different properties as those belonging to class I endochitinases. It was concluded that Cluster-A is the first member of an entirely new class of chitinases in plants. The cluster-A protein was found to be predominantly located intracellularly.

The Cluster-A protein appeared to possess antifungal activity in an in vitro assay against the fungus *Trichoderma viride*. In combination with β-1,3-glucanases this activity was synergistically enhanced as judged from the sensitivity of a number of test fungi. Both lysis and growth inhibition could be detected on *Fusarium solani* and *Alternaria radicina* when Cluster-A protein and β-1,3-glucanase were tested in combination.

The cDNA obtained after screening of the cDNA library with PROB40 was used as a probe to screen a genomic library to isolate the gene encoding the Cluster-A protein. One hybridising clone was characterised and its nucleotide sequence determined. The complete sequence of the cluster-A gene, as well as part of the promoter region, is depicted in FIG. 1. (SEQIDNO: 7). Analysis of the deduced amino acid sequence shows that the Cluster-A protein is probably produced as a larger precursor of which a signal peptide (about 25 amino acids) is cleaved off: the putative cleavage site is indicated by an arrow. Southern analysis (FIG. 2) revealed that the Cluster-A gene is part of a small gene family of about 4 genes.

This novel chitinase, hereinafter referred to as Cluster-A protein, may suitably be used as the active ingredient in antipathogenic, particularly antifungal, compositions, preferably in combination with other proteins with which it works synergistically, such a β-1,3-glucanases. Suitable concentration ranges of Cluster-A protein are from about 0.01 μg/ml to about 100 μg/ml, preferably, from about 0.1 μg/ml to about 10 μg/ml. Antifungal compositions according to the invention may be used in agriculture to combat phytopathogenic fungi in a broad sense; examples are uses in horticulture, arboriculture, ornamental gardening, home gardening, flower culture, and the like. Similarly the antifungal effect of Cluster-A protein may be useful in other industrial areas such as in preservatives for beverages, foods, cosmetics, and the like.

Furthermore, DNA coding for Cluster-A protein, either a cDNA or a genomic sequence, may be cloned behind the regulatory sequences required for expression of the DNA in plants, in order to produce or overproduce Cluster-A protein in plants transformed with the said DNA. The necessary regulatory elements comprise at least a trancriptional initiation region and a translational initiation region functional in plants. Regulatory sequences may include additional elements such as enhancers to promote transcription. Enhancers may increase expression in a constitutive fashion or in a tissue-specific or developmentally, or environmentally regulated fashion.

A preferred mode of expression according to the invention is an essentially relatively constitutive mode of expression, preferably at high levels (for purposes of this invention about 0.1% of soluble protein in leaves is regarded as a relatively high expression level). With a relatively constitutive expression pattern is meant a pattern that is not drastically regulated according to the developmental stage of the plant and which is not tissue-specific. A promoter which is generally regarded by those of skill in the art to be relatively constitutive and not drastically developmentally regulated is the CaMV 35S promoter. A preferred version of such promoter contains a so-called double enhancer. Other relatively constitutive promoters which are suitable to be used in conjunction with the present invention may be obtained from plant viruses (e.g. CaMV 19S promoter, Figwort Mosaic Virus promoter, and the like), as well as from plant genes. Relatively constitutive promoters are also derivable from the T-DNA region of Ti- and Ri-plasmids from Agrobacterium, either or not flanked by transcriptional enhancer sequences. From the literature it is known that the sequence between −343 and −90 of the CaMV 35S promoter increases the activity of the CaMV 35S promoter (Kay R. et al (1987), Science 236, 1299–1302) and presumably also of other constitutive promoters (e.g. mannopine synthase promoter: U.S. Pat. No. 5,106,739).

Examples of light-inducible high-level promoters are the ribulose bisphosphate carboxylase small subunit (rbcSSU) promoter and the chlorophyl a/b binding protein (Cab) promoter, both of which may be used in conjunction with the present invention.

It may be desirable to restrict expression of the introduced chimeric genes to one or a few pre-selected organs or tissues, for instance those that are targets for fungal attack, such as roots, epidermal cells, and the like. A well known example of a tissue-specific promoter is for example the patatin class-II promoter. Also root-specific promoters may be used. Suitable promoters for use in a process according to the invention may also be wound-inducible.

The invention also embraces the use of hybrid promoters, i.e. promoters that comprise elements derived from regulatory elements of different genes.

Plant expressible genes generally comprise a so-called terminator sequence including a polyadenylation signal, it is also possible to use the terminator of the gene according to the invention, this is not critical.

The word 'gene' as used here is meant to comprise cDNAs as well as transcribed region of a genomic sequence, either of which may be synthetic or partially synthetic. If desired codon usage may be changed for use in e.g. monocotyledonous plant hosts, or non-plant hosts. 'Plant expressible gene' shall mean a DNA sequence which is operably linked to regulatory sequences required for transcription in a plant cell and which yields RNA upon transcription which, after processing, can be translated into protein. A gene is 'plant expressible' if it is expressed at least in one tissue in one particular phase of the life cycle of the plant. A gene is understood to be plant expressible even if it is not expressed at all stages during development or only after induction by certain internal or external stimuli.

A plant expressible recombinant DNA sequence according to the invention shall mean to comprise any DNA sequence which at least combines two sequences that are not associated naturally. For instance plant expressible recombinant DNA may comprise genes which comprise combinations of functional regions of a eukaryotic gene such as enhancers, transcription/translation initiation regions, coding regions, non-translated leaders, signal sequences, vacuolar targeting sequences, terminator sequences, introns, exons, and the like, or parts thereof. Any deletion, addition, or substitution of one of those elements yielding an expression level or pattern different from the natural situation is envisaged by the present invention. A modification does not necessarily have to increase expression levels. The present invention for instance clearly envisages the truncation of the C-terminal part of the protein according to the invention in order to redirect its accumulation to the apoplastic (extracellular) space, which may be a preferred location for an antipathogenic protein. Modifications as this truncation may be the only modification of the gene, leaving the remainder of the open reading frame, as the other sequences determining its functioning (such the promoter, terminator, introns and exons, and the like) untouched, yet bring the DNA encoding a protein according to the invention under the definition of a plant expressible recombinant DNA.

An effective site of action of antifungal proteins in the protection of transformed plants against plant pathogenic fungi is believed to be the apoplastic space. Hence, plants may be transformed with a recombinant DNA construct encoding a plant expressible gene according to the invention which exerts its action in the apoplastic space of the plant, either naturally or by virtue of genetic modification.

Genes encoding proteins that naturally occur in the plant cell vacuole are modified such that the C-terminal amino acids involved in vacuolar targeting are not present in the translation product (e.g. by introducing a translational stop-codon in the C-terminal end of the coding region of the gene, or otherwise). The effect of this truncation is targeting of the vacuolar protein to the apoplastic space (for details of the procedure see EP 440 304 A1).

Each of the above mentioned manipulations are well known to those of skill in the art and the effects thereof on expression level, targeting and disease resistance can readily be evaluated using standard techniques.

Generally, transformed plants are evaluated for the presence of the desired properties and/or the extent to which the desired properties are expressed. A first evaluation may include the level of expression of the newly introduced genes, the level of fungal resistance of the transformed plants, stable heritability of the desired properties, field trials and the like.

Secondly, if desirable, the transformed plants can be cross-bred with other varieties, for instance varieties of higher commercial value or varieties in which other desired characteristics have already been introduced, or used for the creation of hybrid seeds, or be subject to another round of transformation and the like.

The combination of Cluster-A protein with tobacco β1,3-glucanase produces a synergistic antifungal effect in vitro. Similarly, a synergistic antifungal effect is expected when both proteins are produced or overproduced in planta. This is deduced from the fact that when combinations of chitinases and glucanases produce a synergistic effect in vitro they do so in vivo as well (EP 440 304 A1)

Examples of proteins that may be used in combination with antifungal proteins according to the invention include, but are not limited to, β1,3-glucanases and other chitinases such as those obtainable from barley (Swegle M. et al, 1989, Plant Mol. Biol. 12, 403–412; Balance G. M. et al, 1976, Can. J. Plant Sci. 56, 459–466; Hoj P. B. et al, 1988, FEBS Lett. 230, 67–71; Hoj P. B. et al, 1989, Plant Mol. Biol. 13, 31–42 1989), bean (Boller T. et al, 1983, Planta 157, 22–31; Broglie K. E. et al. 1986, Proc. Natl. Acad. Sci. USA 83, 6820–6824; V_geli U. et al, 1988 Planta 174, 364–372); Mauch F. & Staehelin L. A., 1989, Plant-Cell 1, 447–457); cucumber (Métraux J. P. & Boller T. (1986), Physiol. Mol. Plant Pathol. 28, 161–169); leek (Spanu P. et al, 1989, Planta 177, 447–455); maize (Nasser W. et al, 1988, Plant Mol. Biol. 11, 529–538), oat (Fink W. et al, 1988, Plant Physiol. 88, 270–275), pea (Mauch F. et al 1984, Plant Physiol. 76, 607–611; Mauch F. et al, 1988, Plant Physiol. 87, 325–333), poplar (Parsons, T. J. et al, 1989, P.N.A.S. 86, 7895–7899), potato (Gaynor J. J. 1988, Nucl. Acids Res. 16, 5210; Kombrink E. et al 1988, Proc. Natl. Acad. Sci. USA 85, 782–786; Laflamme D. and Roxby R., 1989, Plant Mol. Biol. 13, 249–250), tobacco (e.g. Legrand M. et al 1987, Proc. Natl. Acad. Sci. USA 84, 6750–6754; Shinshi H. et al. 1987, Proc. Natl. Acad. Sci. USA 84, 89–93), tomato (Joosten M. H. A. & De Wit P. J. G. M. 1989, Plant Physiol. 89, 945–951), wheat (Molano J. et al, 1979, J. Biol. Chem. 254, 4901–4907), and the like.

The cloning of plant genes corresponding to proteins that can suitably be used in combination with genes encoding antifungal proteins according to the invention and the overexpression of such genes in transgenic plants, as well as the manipultation of expression (including targeting) and the assessment of disease resistance in planta is all within the scope of those of skill in the art, as is exemplified inter alia in Application European patent application 0 440 304 A1, and European patent application 0 460 753 A2. Both applications are herein incorporated by reference.

Transgenic plants which harbor more than one chimeric antifungal gene may be obtained by a variety of processes including the following:

A. the use of one recombinant polynucleotide, e.g. a plasmid, with a number of modified genes physically coupled to one selection marker gene.

B. Cross-pollination of transgenic plants which are already capable of expressing one or more chimeric genes coupled to a gene encoding a selection marker, with pollen from a transgenic plant which contains one or more gene constructions coupled to another selection marker. Afterwards the seed, which is obtained by this crossing, is selected on the basis of the presence of the two markers. The plants obtained from the selected seeds can afterwards be used for further crossing.

C. The use of a number of various recombinant polynucleotides, e.g. plasmids, each having one or more chimeric genes and one other selection marker. If the frequency of co-transformation is high, then selection on the basis of only one marker is sufficient. In other cases, the selection on the basis of more than one marker is preferred.

D. Consecutive transformations of transgenic plants with new, additional chimeric genes and selection marker genes.

E. Combinations of the above mentioned strategies. The actual strategy is not critical with respect to the described invention.

Any plant species that is subject to some form of fungal attack may be provided with one or more plant expressible gene constructs according to the invention. Likewise any plant subject to some for of fungal attack may be treated with a composition comprising an antifungal protein according to the invention.

Hence, "plants" for the purpose of this invention shall mean gymnosperms as well as angiosperms, dicotyledonous plants as well as monocotyledonous plants, be they used in agriculture, horticulture, forestry, (indoor) gardening, or any other form of activity involving plants, either for direct use as food or feed, or for further processing in any kind of industry, for extraction of substances, for decorative purposes, propagation, cross-breeding, or any other use.

In principle any transformation method may be used to introduce a plant expressible gene according to the invention into a plant species of choice. Generally, useful methods are the calcium/polyethylene glycol method for protoplasts (Krens, F. A. et al, 1982, Nature 296, 72–74; Negrutiu I. et al, June 1987, Plant Mol. Biol. 8, 363–373), electroporation of protoplasts (Shillito R. D. et al, 1985 Bio/Technol. 3, 1099–1102), microinjection into plant material (Crossway A. et al, 1986, Mol. Gen. Genet. 202, 179–185), (DNA or RNA-coated) particle bombardment of various plant material (Klein T. M. et al, 1987, Nature 327, 70), infection with viruses and the like.

In a preferred embodiment of the invention use is made of Agrobacterium-mediated DNA transfer. Especially preferred is the use of the so-called binary vector technology as disclosed in EP-A 120 516 and U.S. Pat. No. 4,940,838).

Generally, after transformation plant cells or explants are selected for the presence of one or more markers which are encoded by plant expressible genes co-transferred with the plant expressible gene according to the invention, whereafter the transformed material is regenerated into a whole plant.

Although considered somewhat more recalcitrant towards genetic transformation, monocotyledonous plants are amenable to transformation and fertile transgenic plants can be regenerated from transformed cells or protoplasts. Presently, preferred methods for transformation of monocots are microprojectile bombardment of explants or suspension cells, and direct DNA uptake or electroporation (Shimamoto, et al, 1989, Nature 338, 274–276). Transgenic maize plants have been obtained by introducing the *Streptomyces hygroscopicus* bar-gene, which encodes phosphinothricin acetyltransferase (an enzyme which inactivates the herbicide phosphinothricin), into embryogenic cells of a maize suspension culture by microprojectile bombardment (Gordon-Kamm, 1990, Plant Cell, 2, 603–618). The introduction of genetic material into aleurone protoplasts of other monocot crops such as wheat and barley has been reported (Lee, 1989, Plant Mol. Biol. 13, 21–30). Wheat plants have been regenerated from embryogenic suspension culture by selecting only the aged compact and nodular embryogenic callus tissues for the establishment of the embryogenic suspension cultures (Vasil, 1990 Bio/Technol. 8, 429–434). The combination with transformation systems for these crops enables the application of the present invention to monocots.

Monocotyledonous plants, including commercially important crops such as corn and rice are readily amenable to transformation by Agrobacterium strains (Gould J, Michael D, Hasegawa O, Ulian E C, Peterson G, Smith R H, (1991) Plant. Physiol. 95, 426–434) Hiei Y et al. (1994) Plant Journal 6, in press.

Plants and plant parts producing or over-producing a novel chitinase according to the invention, either alone or in combination with other antifungal genes, or genes encoding proteins which work synergistically with the chitinase according to the invention, may used to evaluate pathogen resistance, in particular fungal resistance. Subsequently, the more resistant lines may be used in breeding programs to yield commercial varieties with enhanced pathogen, in particular fungal resistance.

Plants with reduced susceptibility against pathogen or fungal attack, may be used in the field or in greenhouses, and subsequently be used for animal feed, (direct) consumption by humans, for prolonged storage, used in food- or other industrial processing, and the like. The advantages of the plants, or parts thereof, according to the invention are a lesser need for fungicide treatment, lowering costs of material, labour, and environmental pollution, or prolonged shelf-life of products (e.g. fruit, seed, and the like) of such plants.

Furthermore, post-harvest losses may be reduced due to the presence of enhanced levels of the chitinase according to the invention as well.

Further advantages of the invention not explicitly mentioned here may occur to those of skill in the art and such advantages do not depart from the true scope of the invention.

The following Examples merely serve to further illustrate the invention and these examples or any statements made therein should not be construed as a limitation of the scope of the invention.

EXAMPLE 1

Isolation of a cDNA Corresponding with Cluster-A

Cluster-A mRNA was reported to be strongly induced after TMV-infection of *Nicotiana tabacum* cv. Samsun NN (Hooft van Huijsduijnen et al, 1986, supra). Screening of a lambda ZAP cDNA library (see EXPERIMENTAL part) of TMV-infected Samsunn NN tobacco plants with a probe derived from PROB40 (a partial Cluster-A cDNA clone) resulted in the isolation of 11 positively hybridizing clones. Restriction enzyme analysis and (partial) sequence analysis revealed that all clones were identical. It was concluded that the clones correspond to Cluster-A cDNA. The nucleotide sequence of one of these clones (cA-3) was determined (EXPERIMENTAL PART) and is depicted in SEQIDNO: 1 and 2. This clone lacks in 7 codons of the 5' part of the open reading frame.

EXAMPLE 2

Cloning of a Complete cDNA Clone in a Bacterial Expression Vector

The cDNA clone was completed by performing a PCR reaction (EXPERIMENTAL PART) on clone cA-3 with the following primer T7: 5'-AATACGACTCACTATAG-(SEQIDNO: 3) and primer p1: 5'-GTTTCCTTCTCCATGGAACTAGTTTGCAC (SEQIDNO: 4).

After digestion of the PCR-amplified product with restriction enzymes NcoI and XhoI, electrophoresis and isolation of the fragment from an agarose gel, it was ligated into an intermediate NcoI/XhoI-digested vector pGV84, followed by transformation of *E. coli* DH5α. The NcoI/XhoI fragment from positive clones resulting from this transformation was subsequently ligated into a NcoI/SalI-digested bacterial expression vector (pJLA602, Medac, Hamburg, Germany) and used to transform *E. coli* DH5α. Positive transformants, were screened by hybridization to the labeled clone cA-3 and the presence of the correct size and orientation of the insert was determined by restriction enzyme analysis. The resulting plasmid, pJLA-A53 contains the putative Cluster-A open reading frame (ORF), including codons 20–377, downstream of a tandem arrangement of the repressible $p_R$ and $p_L$ promoters of phage lambda and a highly efficient *E. coli* translational initiation region. Finally, plasmid pJLA-A53 was used to transform *E. coli* strain KA1092 (trp65, lon, sFiA-1, malB) (Johnson, B. F. et al, 1977, Mol. Gen. Genet. 157, 91–97) [protease−]. This strain was used to produce Cluster-A protein and to generate antibodies. Strain KA1092, harbouring pJLA-A53, has been deposited at the Centraal Bureau voor Schimmelcultures, on Aug. 12, 1993, accession number CBS 415.93).

EXAMPLE 3

Figure 5:
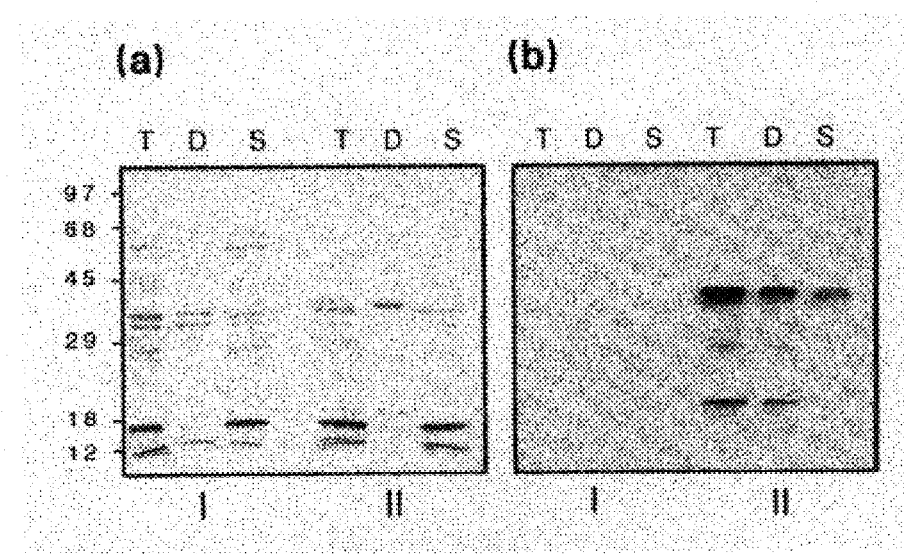
FIGS. 5A and 5B. Over-production of Cluster-A in *E. coli*. (A): On a 12.5% SDS-polyacrylamide gel different samples, total fraction (T), cell debris (D) and soluble fraction (S), were analyzed. (B): Immunoblot analysis of an identical protein gel with specific detection of Cluster-A proteins.

Expression of a Clu-A cDNA in *E. coli* and Generation of Antibodies Against the Putative Clu-A Protein The Cluster-A cDNA gene, codons 20–377 was placed under the control of the lambda $p_R$ and $p_L$ promoters (Schauder B. et al., 1987, Gene 56, 279–283), in order to overexpress the gene in *E. coli*. In FIG. 5 is shown the overproduction of the putative 40 kDa Cluster-A protein in *E. coli* strain KA1092. After disrupting the cells by sonification, Cluster-A protein aggregates were isolated by centrifugation with the cells debris (FIG. 5, lane D). Expression of the putative Cluster-A cDNA gene was induced in KA1092 by switching cultures grown for 3 h at 30° C. to a waterbath at 42° C. and incubating for another 3 h. Bacteria were collected by centrifugation and dissolved in 1/25 vol. of sample buffer (25 mM Tris, 192 mM glycine, 6 M urea, 2.5% SDS, 10% glycerol, 5% β-mercapto-ethanol). The putative Cluster-A protein produced in *E. coli* was purified and used for the generation of antibodies (EXPERIMENTAL PART).

FIG. 5 shows a Western blot analysis of similar protein fractions shown in FIG. 5 and demonstrates that the isolated antibodies are specifically directed against the putative Cluster-A protein. A strong signal for Cluster-A protein is found in the total fraction (lane T) and cell debris fraction (lane D) of induced *E. coli* cells which contained the Cluster-A expression construct. The weak signal found in lane S, indicates that a minor amount of the Cluster-A protein is present in the soluble protein fraction.

After heating for 3 min at 100° C., the samples were electrophoresed in SDS-polyacrylamide gel (EXPERIMENTAL PART) and proteins were visualized by staining with Coomassie Brilliant Blue. Similar gels were stained with icecold 1 M KCl and the regions of the gel containing the overproduced 40 kDa proteins were cut out. After washing in water, the acrylamide was ground and mixed with Freunds complete immunization medium, upon which a suspension with about 200 ng putative Cluster-A was injected subcutaneously into rabbits. After three additional immunizations at two-week intervals with similar suspensions in Freunds incomplete medium, 50 ml blood was collected from the rabbits and the serum fraction was tested for antibodies directed against the putative Cluster-A protein.

EXAMPLE 4

Isolation and Characterization of Putative Cluster-A Protein from Tobacco

The purification of the putative Cluster-A protein from TMV infected tobacco leaves (EXPERIMENTAL PART) was monitored by immunodetection using the antiserum obtained as described in EXAMPLE 3.

The putative Cluster-A protein appeared to absorb to a cation-exchanger S-Sepharose indicating a basic nature of the protein. No cross-reacting proteins were observed in the flow-through of the S-Sepharose column. The putative Cluster-A protein was eluted from the S-Sepharose column in the presence of 75 to 140 mM NaCl. Close examination of the SDS-polyacrylamide gels and immunoblots revealed that two proteins of about the same molecular weight (41 kDa and 43 kDa) cross-reacted to the antiserum. Apparently, both proteins were related. The presence of potential glycosylation sites in both the cDNA sequence (3 potential glycosylation sites) and the gDNA sequence (4 potential glycosylation sites) prompted us to study the binding of the putative Cluster-A protein to Con-A Sepharose. Proteins were, therefore, dialysed to 50 mM Tris, HCl, pH 6.8, containing 1.15 M NaCl and allowed to absorb to Con-A Sepharose. Most of the 41 kDa Cluster-A protein passed through the Con-A column while among the bound proteins the 43 kDa putative Cluster-A protein was present, indicating that this latter protein is at least partly glycosylated. Con-A Sepharose was not applied in the purification of the putative Cluster-A protein. Instead, chelating Sepharose chromatography was used. The fractions containing the putative Cluster-A protein eluting from the S-Sepharose column were dialysed against 50 mM Tris, HCl buffer pH 8.0, containing 150 mM NaCl and allowed to absorb to a chelating Sepharose column activated with $Zn^{2+}$ ions and equilibrated in the above buffer. About 20% of the total amount of protein was retarded by the activated matrix and appeared to consist mainly of Cluster-A protein. Second passage through the chelating Sepharose column resulted in an almost pure protein preparation (FIG. 5, lane D). The putative Cluster-A protein was purified to homogeneity by subsequent gelfiltration chromatography. The apparent native molecular weight was between about 40 and 43 kDa.

EXAMPLE 5

Elucidation of the Amino Acid Sequence of the Putative Cluster-A Proteins

A mixture of both 41 kDa and 43 kDa Cluster-A protein was separated on a 12.5% SDS-polyacrylamide gel and electroblotted to a PVDF membrane. The mixture was then used to determine the N-terminal amino acid sequence by Edman degradation (EXPERIMENTAL PART). However, the N-terminus was blocked and no sequence information was obtained. The presence of a unique site susceptible for acid hydrolysis enabled us to determine an internal sequence from the same material:

P-V-N-H-X1-S-G-S-D-X2-I-N-A-X3-I-Q (SEQ ID NO: 4).

X1 = V/I, X2 = G, X3 = W,

The amino acid preceding this sequence is most probably an Asp (D) residue since the digestion used is specific for Asp-Pro bonds (Landon 1977, sub). Additional sequence information was obtained after cleaving the putative Cluster-A protein with hydroxylamine. This resulted in the formation of two peptides of about the same molecular weight which were blotted together onto a PVDF membrane. Sequencing of this sample yielded the following sequences:

(SEQ ID NO: 5)
G-L-N-Y-P-V-E-S-V-A-R-N-L-N-W, and:

(SEQ ID NO: 6)
S-H-A-Q-L-F-D-P-V-N-H-X-S-G-S-

D-G-I-N-A-W-I-Q-A-G-V, wherein X = I/V.

These peptide sequences showed complete identity to the amino acid sequence deduced from the cDNA clone (FIG. 1; SEQIDNO: 1 and 2). It was concluded from these matching data that the two proteins purified from tobacco correspond to the protein produced by *E. coli* KA1092 transformed with the partial Cluster-A ORF. The peptide sequence, corresponding to codon position 233, showed that two amino acids (V/I) were present at this position in a 1:1 ratio.

Possibly two highly identical Cluster-A proteins were purified and differ for one amino acid position in the region sequenced.

Figure 4:
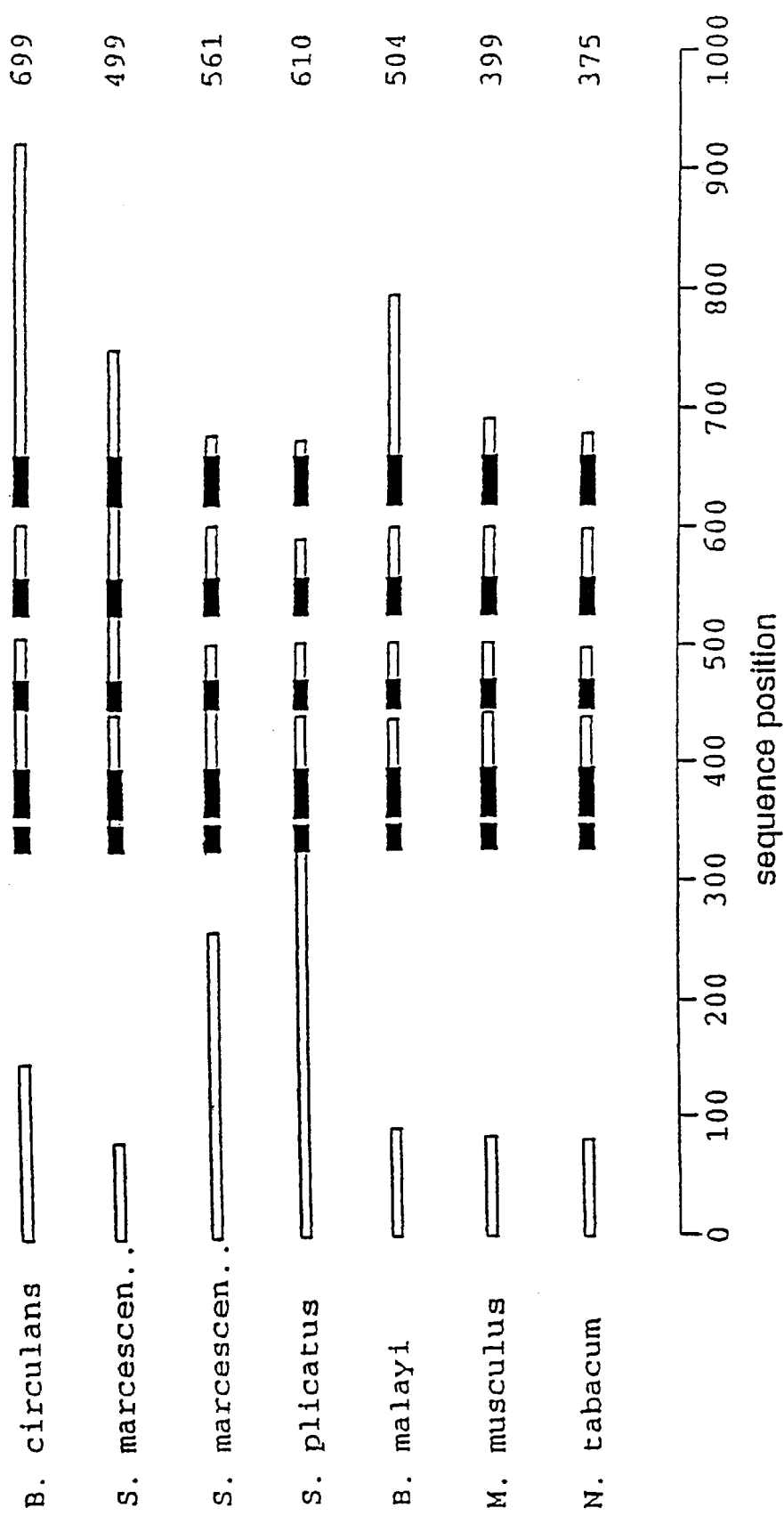
FIG. 4. Alignment of Cluster-A of Nicotiana tabacum with exo-chitinases from *Bacillus circulans, Serratia marcescens, Streptomyces plicatus, Brugia malayi* (nematode) and *Mus musculus* (mouse). The black boxes indicate regions with a high degree of identity according to the multiple alignment analysis by Schuler G. D. et al, 1991, Protein Struct. Funct. Genet. 9, 180–190).

Comparison of the Cluster-A protein with matching proteins in a database revealed homology with the bacterial chitinases ChiA and ChiB from *Bacillus circulans* and *Serratia marcescens*, respectively. Although the overall identity of Cluster-A to ChiA (31%) and ChiB (26%) is low, specific regions are highly conserved within all three amino acid sequences, as shown in FIG. 4. In addition, homology was found with chitinases from *Streptomyces plicatus, Brugia malayi* (nematode), and a secretory protein from *Mus musculus* (Murinae). No structural homology was found with the four distinct classes of plant chitinases (Lawton K. et al, 1992, Plant Mol Biol. 19, 735–743; Collinge, 1993, supra).

EXAMPLE 6

Enzymatic Activities and Cellular Localization of Cluster-A

The homology of the tobacco Cluster-A protein with bacterial chitinases suggested that this protein might be able to catalyze the hydrolysis of chitin, a $\alpha$-1,4-linked polymer of N-acetyl-D-glucosamine. The possibility to purify Cluster-A protein from tobacco material, using the antibody enabled us to test this hypothesis. Cluster-A was tested for chitinase activity. In an endo-chitinase assay, using tritiated chitin as a substrate (Molano J. et al, 1977, Anal. Biochem. 83, 648–656), the Cluster-A protein showed a specific activity of 40±6 cpm per $\mu$g protein, which is about 250 to 500 fold lower than the specific activities of the class-I chitinases (Legrand M. et al, 1987, Proc. Natl. Acad. Sci. USA 84, 6750–6754; Sela-Buurlage M. B. et al, 1993, Plant Physiol. 101, 857–863). However, chitinase activity of Cluster-A measured by a colorimetric assay, using a soluble chitin dye substrate (Wirth and Wolf, 1990, J. Microbiol. Methd. 12, 197–205), was two-fold higher than that of class-I chitinase (Table 1). Testing of Cluster-A for additional enzyme activities indicated that this protein possessed no exo-chitinase activity, chitobiase, $\beta$-1,3-glucanase or lysozyme activity.

Figure 6:
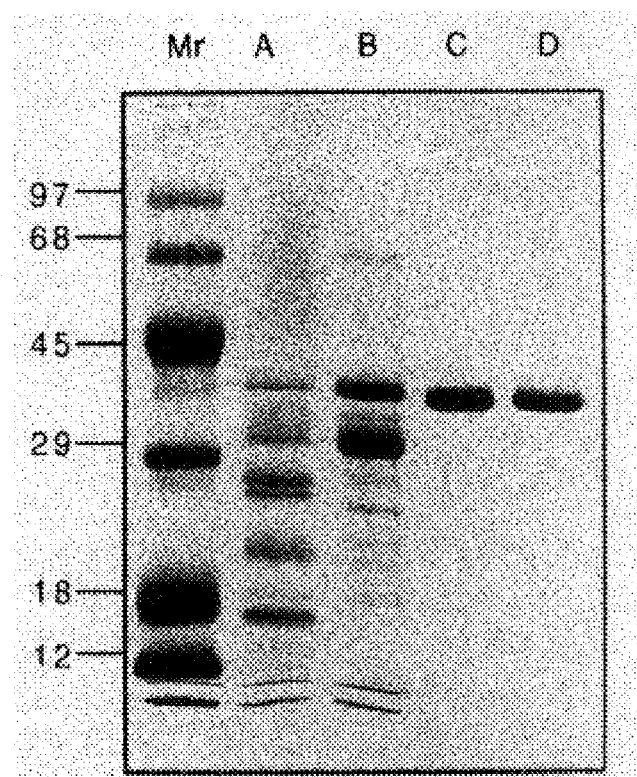
FIG. 6. Purification of the Cluster-A protein from TMV-infected tobacco leaves. SDS-polyacrylamide gel shows the protein profile of different purified fractions. A: sample of desalted crude leaf-extract, B: protein pool after S-sepharose cation-exchange chromatograph, C: protein pool after Chelating Superose column, D: purified Cluster-A after gel-filtration chromatography. The lane "Mr" shows pre-stained markers with molecular weights as indicated.

The cellular localization of Cluster-A was analyzed using different leaf fractions of TMV infected tobacco plants, including (a) total leaf fraction, (b) leaf material from which the extracellular fluid (EF) was removed, and (c) the EF-fraction. Western analysis indicated that Cluster-A proteins are predominantly located intracellularly, as shown in FIG. 6. A strong signal for Cluster-A protein was found in fraction-a and fraction-b. In the extracellular fluid of TMV infected leaves no Cluster-A protein was found (fraction-c).

TABLE 1

Chitinase activities of Cluster-A proteins
Chitinase activities (expressed per $\mu$g)

| Protein | $^3$H-chitin assay | CM-chitin assay |
|---|---|---|
| PR-3a (PR P) | 1180 ± 57 cpm | 36.2 ± 1.10 ODe |
| PR-3b (PR Q) | 1087 ± 35 cpm | 30.9 ± 1.90 ODe |
| 32 kDA (Chi-I) | 11471 ± 347 cpm | 1.0 ± 0.03 ODe |
| Cluster-A | 40 ± 6 cpm | 2.1 ± 0.03 ODe |
| exochitinase # | 746 ± 60 cpm | 7.0 ± 0.34 ODe |

CM-chitin, carboxymethyl-chitin bound to Remazol Brilliant Violet
& Tritiated chitin substrate (Molano et al, 1977)
$ p-nitrophenyl liberation assay, substrate p-nitrophenyl chitobiose (Roberts and Selitrennikoff, 1988).
exochitinase from *S. griseus* (Sigma C-1650).

The exochitinase activity of all chitinases was tested with the p-nitrophenyl liberation assay with p-nitrophenyl chitobiose as substrate, according to (Roberts W. K. and Selitrennikoff C. P., 1988, J. Gen. Microbiol. 134 169–176). For PR-3a, PR-3b, 32 kDa Chi-I, and Cluster-A the amount of liberated p-nitrophenyl was less than 0.05 nmole as opposed to 4.50+0.1 nmole for the exo-chitinase (not shown in the table). All assays were performed at 37° C. and pH 6.0. Incubation times were usually 30 minutes but in case of low lysozyme activities these incubations were prolonged. The specific activity is expressed as cpm liberated, and blue substrate liberated measured as an increase of OD, respectively.

EXAMPLE 7

Antifungal Activity of Cluster-A Protein in vitro

Figure 7:
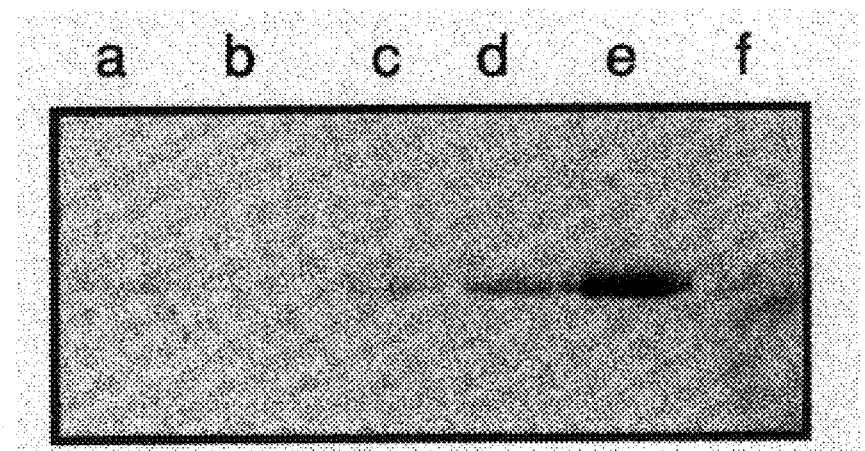
FIG. 7. Cellular localization of Cluster-A. The antiserum to the Cluster-A protein was used to determine the cellular localization of tobacco Cluster-A. Healthy non-infected and TMV-infected tobacco plants were analysed. Samples of a total protein fraction (lane a), leaf fraction without extracellular washing fluid (lane b), and EF-fraction (lane c), were separated on a 12.5% SDS-gel and electroblotted to a PVDF membrane, and used for detection of Cluster-A proteins.
Figure 8:
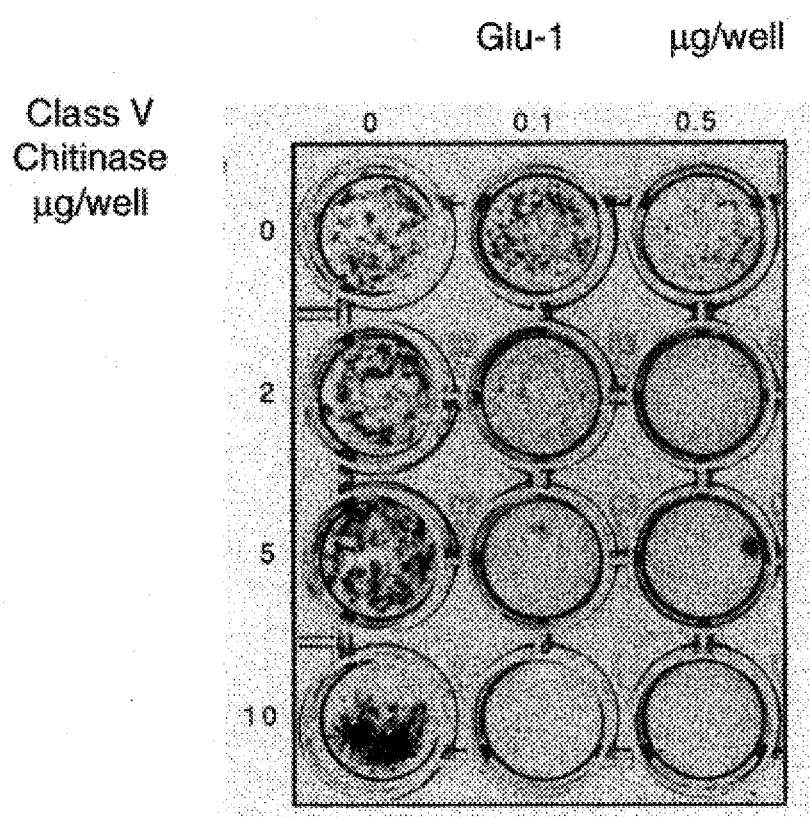
FIG. 8. Growth inhibition of *Fusarium solani* by the synergistic activity of Cluster-A and class I $\beta$-1,3-glucanase proteins. The effect of Cluster-A on fungal growth in vitro was tested by the addition of Cluster-A to pre-germinated spores of *Fusarium solani*, either alone, or in combination with class I $\beta$-1,3-glucanases. Amounts of protein (in $\mu$g) per well are indicated. After three days of incubation at 20° C. the fungal mycelia were visualised by staining with lactophenol cotton blue.

In previous reports it has been demonstrated that class-I chitinases (Chi-I) and $\beta$-1,3-glucanases (Glu-I) can inhibit fungal growth in vitro (Mauch et al, 1988; Sela-Buurlage et al, 1993). Both hydrolytic enzymes have been implicated to play an important role in the defense mechanisms of plants against invading fungi. The antifungal activity of Cluster-A was investigated by testing the lysis activity of this protein alone or in combination with Chi-I or Glu-I on different fungi. Cluster-A protein alone caused lysis and growth inhibition of Trichoderma viride at a concentration of 12 $\mu$g/ml. On the phytopathogenic fungus *Alternaria radicina* Cluster-A inhibited fungal growth at 30 to 60 $\mu$g/ml. Even at high concentrations (600 $\mu$g/ml) no effect was found on *Fusarium solani*. However, Cluster-A protein exhibited on *F. solani* a potent antifungal effect in synergy with the class I $\beta$-1,3-glucanase (and chitinase) proteins. The synergistic action of these proteins caused both lysis of pregerminated spores and growth inhibition of *F. solani*, see FIG. 7. The Cluster-A protein exhibited no effect on te phytopathogenic fungi *Septoria lycopersici* and *Phytophthora infestans* (data not shown).

TABLE 2

Antifungal activity of Cluster-A protein:
Lysis activity of Cluster-A on *Fusarium solani* and *Alternaria radicina*.

| | *Fusarium solani* | | | | *Alternaria radicina* | | | |
|---|---|---|---|---|---|---|---|---|
| Cluster A | Chi-I | | Glu-I | | Chi-I | | Glu-I | |
| $\mu$g/well | 0 | 0.1 | 0.5 | 0.1 | 0.5 | 0.1 | 0.5 | 0.1 | 0.5 |
| 0 | 0 | 0 | 0 | 5 | 56 | 0 | 0 | 42 | 54 |
| 2 | 0 | 0 | 0 | 26 | 95 | 0 | 0 | 45 | 34 |
| 5 | 0 | 0 | 5 | 34 | 95 | 0 | 0 | 45 | 38 |
| 10 | 0 | 0 | 5 | 95 | 95 | 0 | 0 | 35 | 30 |
| 10 den. | 0 | — | — | — | — | — | — | — | — |

TABLE 3

Antifungal activity of different protein preparations expressed in % lysis and growth inhibition (Gl).

| | | *Fusarium solani* | | *Alternaria radicina* | |
|---|---|---|---|---|---|
| protein | protein added ($\mu$g/well) | % lysis | GI | % lysis | GI |
| Clu-A | 5–10 | 0% | 0 | ND | 4 |
| Clu-A | 100 | 0% | 0 | ND | ND |
| Glucanase | 0.1 | 0% | 0 | ND | ND |
| Clu-A + Gluc. | 10:0.1 | 0% | 2–3 | ND | ND |
| Chitinase | 0.1 | 0% | 0 | ND | ND |
| Clu-A + Chit. | 10:0.1 | 5% | 1 | ND | ND |

Data for the denatured control samples are given in brackets but only in case they differ from 0% lysis and/or Gi=0.

EXAMPLE 8

Isolation of a Genomic Clone Encoding Cluster-A Protein

A genomic library of N. tabacum was screened using the Cluster-A cDNA insert of clone cA-3 as a probe. Three recombinant lambda phages, each containing different restriction fragments hybridizing to the Cluster-A cDNA, were purified. The genomic Cluster-A homologous to cA-3 was amplified by a polymerase chain reaction using specific oligonucleotide primers corresponding to the 5' end coding region LS42:

(SEQ ID NO: 10)
5'-TCTCCGGCAACTAGTTTGCAC-3'.

and 3'end non-coding region of the Cluster-A cDNA LS42:

(SEQ ID NO: 11)
5'-GTCATAGTTCACATATCTGTTGCC-3'.

Figure 3:
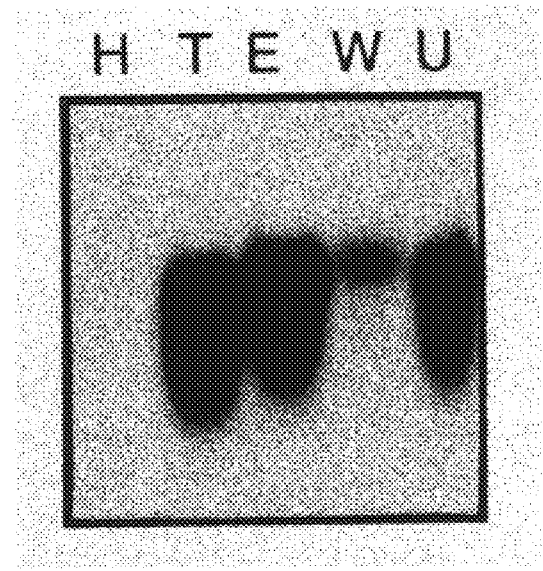
FIG. 3. Northern blot analysis of the tobacco Cluster-A mRNAs upon different forms of stress. Equal amounts of total RNA isolated from non-stressed healthy tobacco leaves (H) or from leaves infected with TMV (T), sprayed with eptephon (E), wounded by cutting (W) or irradiated with UV-light (U) were hybridized to a Cluster-A cDNA probe.

Only one of the three phages showed a very strong amplification of specific sequences with these primers and was selected for further analysis. The complete nucleotide sequence of the Cluster-A cDNA, including the deduced primary structure of the Cluster-A protein and sequences of the 5'-flanking and 3'-flanking regions of the gene, are shown in SEQIDNO: 7 and 8. Comparison of the cDNA clone with the Cluster-A gene revealed that these sequences share a high degree of identity (94%). Within the 5' end upstream region a 'CAAT' motif (position 391) and 'TATAAT' motif (position 428) is found. In the 3' end non-coding region a potential polyadenylation signal (5'-AATAAA-3') is present at position 2971. The coding region of the Cluster-A gene is contained in two exons and yields a precursor protein of 377 amino acids. The Cluster-A precursor protein contains a putative signal peptide of 25 amino acids that is involved in transport across the membrane of the endoplasmatic reticulum, as well as 4 potential N-linked glycosylation sites (N-X-S/T). The predicted mature protein has a calculated molecular weight of 39,033 Da. The intervening sequences of 952 bp and 349 bp in length are present after codon 151 and 364 respectively. To assess the number of genes ecoding Cluster-A like proteins in tobacco, a genomic Southern blot was probed with the cDNA clone. The pattern of bands hybridizing to the probe under stringent conditions shows that Cluster-A is part of a small gene family with at least four different members (FIG. 2). To determine the induction of Cluster-A gene expression, tobacco plants were treated with different stress conditions and analysed on a Northern blot. Samples of different treatments were taken 3 days after inoculation with TMV, 2 days after wounding, 1 day after ethephon treatment, and 1 day after UV-light irradiation. At these time points maximal expression of the PR genes (PR-1 to PR-5) was reported previously by Brederode and coworkers (1991, Plant Mol. Biol. 17, 1117–1125) and was used here to study Cluster-A gene expression. FIG. 3 shows that in non-stressed tobacco leaves there is no detectable expression of the Cluster-A gene. TMV infection of tobacco leaves with ethephon, to produce ethylene, or UV-light resulted both in a high increase of Cluster-A mRNA (FIG. 3, lane E and U). In contrast, a low induction of Cluster-A expression was found after wounding the leaves. These results together indicated that Cluster-A can be classified as a novel pathogenesis-related gene of tobacco.

EXAMPLE 9

Construction of Expression Construct and Binary Vectors

The Cluster-A gene is cloned as an approximately 5.5 kb SstI-fragment. The entire open reading frame is located on this fragment occupying about two third of the fragment; the 5' end of the open reading frame starts at about position 453 from one SstI site. Using PCR a BamHI site is introduced just upstream of the 5' end of the ORF as follows. The original sequence (FIG. 1) (position 406) 5'-TTTAAACTCGAAGTCACAAATTAAA-3' (SEQIDNO: 12) (position 432) is modified into (position 406) 5'-TTTAAACTCGGATCCACAAATTAAA-3' (SEQIDNO: 13) (position 432).

Figure 9:
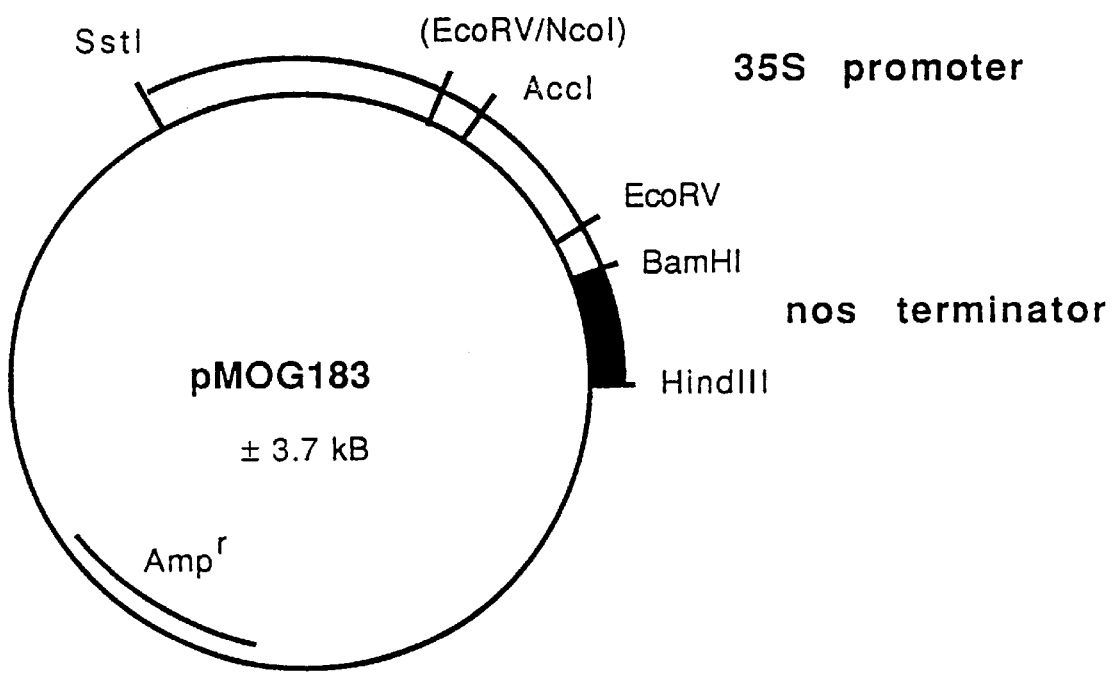
FIG. 9. Schematic representation of vector pMOG183, a derivative of pMOG181 wherein the EcoRI recognition site is replaced by a SstI site this vector is freely available from MOGEN International N.V. upon request.
Figure 10:
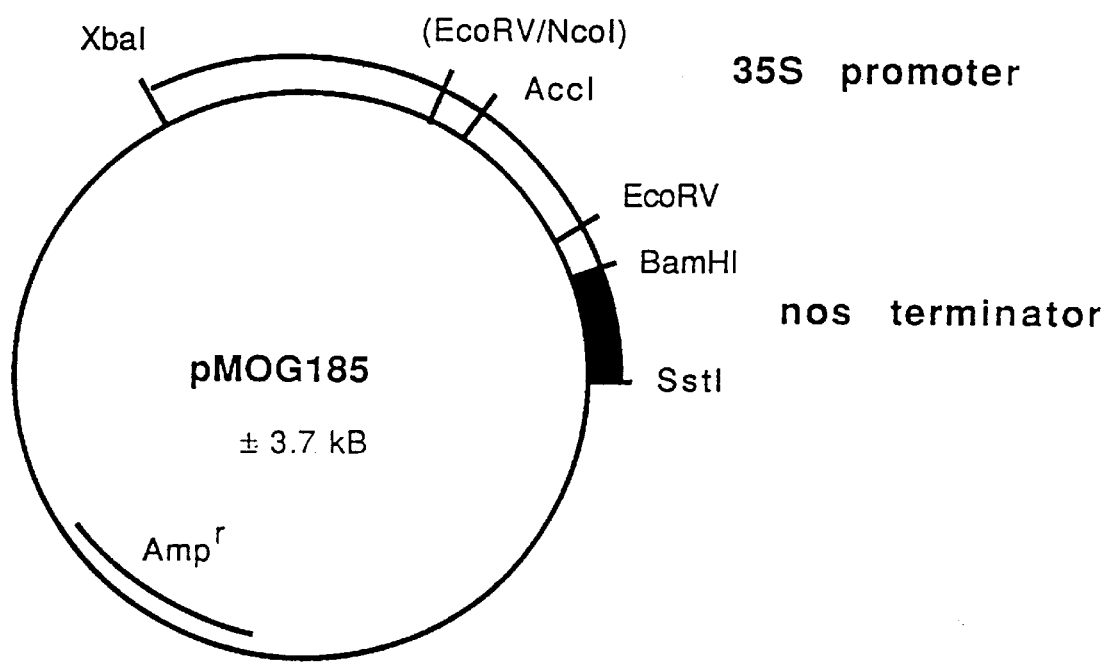
FIG. 10. Schematic representation of vector pMOG185, a derivative of pMOG183 wherein the EcoRI recognition site changed into a XbaI recognition site.
Figure 11:
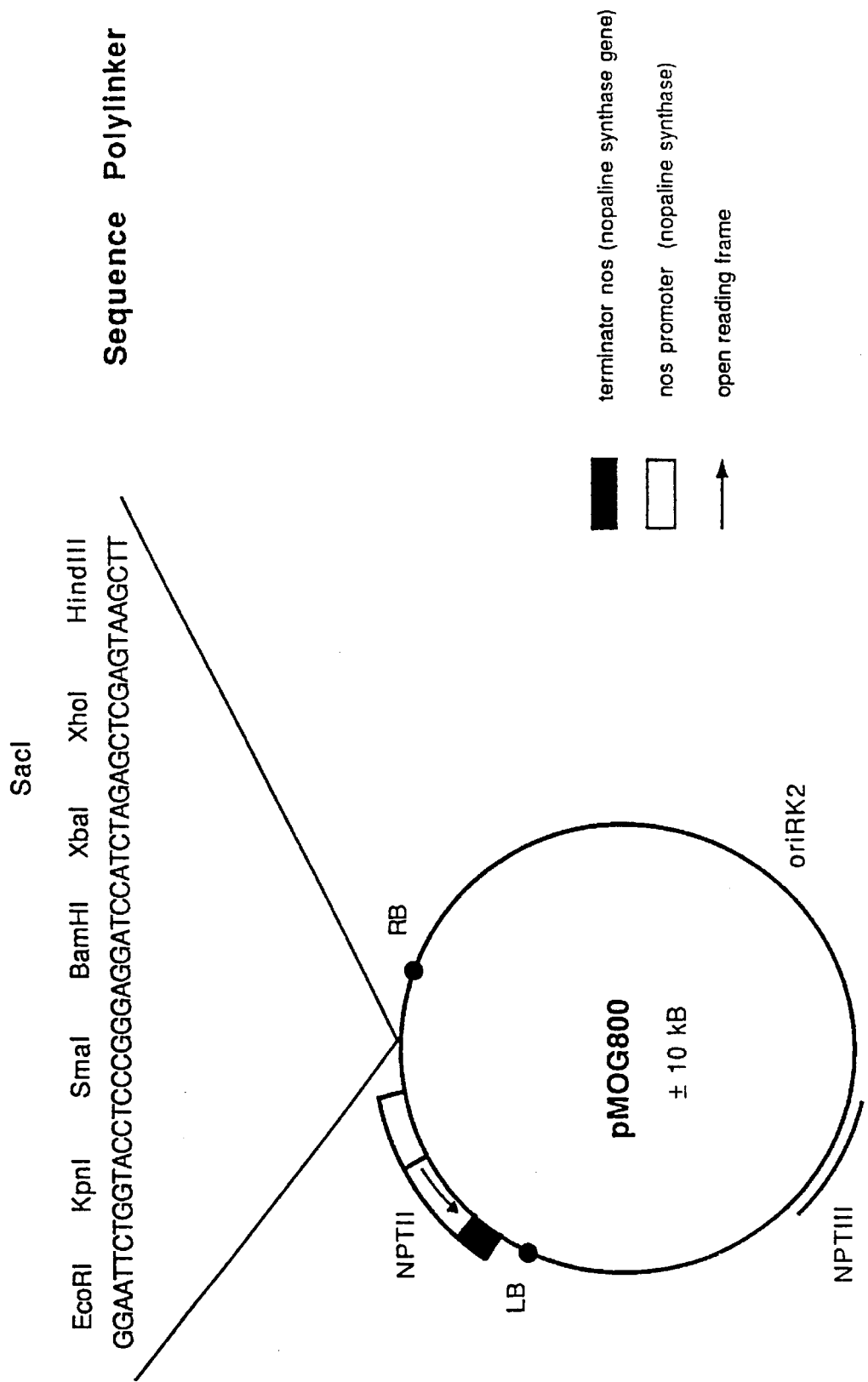
FIG. 11. pMOG800: A suitable binary vector for Agrobacterium-mediated plant transformation, containing a plant expressible kanamycin resistance gene for selection of transformants and a multiple cloning site for insertion of expression cassettes.

Similarly, the EcoRI site in pMOG183 (FIG. 9) is modified into a XbaI-site using the following adaptor sequence in a PCR reaction: 5'-AATTGTCTAGAC-3' (SEQIDNO: 14). The modified cloning vehicle is named pMOG185 and contains the CaMV 35S promoter and the nos-terminator and the BamHI-site for inserting the Cluster-A gene in between. To this end the open reading frame of the Cluster-A gene is cloned as an approximately 5.1 kb BamHI-SstI site, employing the newly created BaMHI site of the Cluster-A fragment, into the BamHI site of modified expression vector pMOG185. The Cluster-A gene flanked upstream by the 35S CaMV promoter with double enhancer, and downstream by the nos-terminator, is now located on a XbaI-SstI fragment. This fragment is subsequently cloned into binary vector pMOG800 (FIG. 10). Binary vector pMOG800 contains a plant expressible kanamycin resistance gene between a left and right T-DNA border, as well as a multiple cloning site for insertion of restriction fragments. An E. coli strain harbouring this vector has been deposited on Aug. 12, 1993, at the Centraal Bureau voor Schimmelcultures, Baarn, The Netherlands, No. CBS 414.93) with the aid of the suitable synthetic double-stranded, partially complementary, adapter sequences (e.g. 5'-AGCTCACG-3' and 3'-GTGCTTAA-5'). The binary vector so obtained contains both a essentially constitutively expressible Cluster-A gene and a plant expressible NPTII gene as marker, localized between the left and right T-DNA border sequences.

With the aid of plasmid pRK2013, this pMOG800 derived binary vector is then mobilised from E. coli DH5α into Agrobacterium tumefaciens strain MOG101 harbouring a helper plasmid with the Vir-functions. The transconjugants are isolated from these matings on selection medium containing 40 mg/l rifampicin, 250 mg/l spectinomycin, and 100 mg/l kanamycin. (for details see EXPERIMENTAL PART). The Agrobacterium cells having received the binary vector are used for the transformation of plants.

EXAMPLE 10

Tansformation of Plants and Analysis of Expression a. tomato

The transformation of tomato (Lycopersicon esculentum cv. Moneymaker) with Agrobacterium strains MOG101 harbouring the pMOG800 derived binary vector is performed essentially as described by McCormick et al (1986, Plant Cell Rep. 5, 81–84).

b. tobacco

For the transformation of tobacco use is made of the leaf-disc dip method (1985, Horsch et al, Science 227, 1229–1231). Leaf-discs are cocultivated with Agrobacterium strain MOG101 harbouring the binary vector and grown on selection medium with 100 mg/ml kanamycin. The transgenic shoots are regenerated into whole plants and analyzed for expression of the newly introduced genes. For this analysis use is made of Western blots, using the antiserum against the Cluster-A protein and/or glucanase.

c. potato cv. Kardal

Potato tubers must be stored at +4° C. 7 days before transformation the tubers must be transferred to room temperature.

Day 1. Inoculate Agrobacterium strain from fresh plate into 10 ml LB+100 mg/l Kanamycin+20 mg/l Rifampicillin. Grow overnight by 29° C.

Day 2. Dilute Agrobacterium suspension 1:10 in Minimal Medium+100 mg/l Kanamycin; Grow overnight by 29° C. Poor plates with medium 1.

Day 3. Dilute Agrobacterium suspension to $OD_{600} \pm 0.15$ in Minimal Medium without antibiotics and grow to $OD_{600}$ 0.30–0.70. (this takes about 4 hours).

Spin culture down and make a 1:10 dilution in $MS_{30}R3$. Peel the potatoes.

Wash 1 minute with ethanol 70%.

Wash 20 minutes in 1:5 diluted Teepol+0.1% Tween 20.

Wash once with sterile water.

Add±100 ml 1:1 mixed RK:KI (Blue color must stay for 2 minutes).

Wash the blue color away with sterile water.

Cut tubers in slices of about 2 mm thickness.

Cut with bore little disks of the vascular tissue.

Collect the discs in large petridishes (15 cm) with liquid $MS_{30}R3$ (about 400 per dish).

Dry 40 disks on sterile filterpaper and place them on medium 1 as contril (2 dishes).

Remove $MS_{30}R3$ medium with a pipet and replace it for the *Agrobacterium mox.*

Replace after 20 minutes the Agrobacterium suspension for liquid $MS_{30}R3$.

Dry disks on sterile filterpaper and transfer them to Petridishes with medium 1 (20 disks per plate).

Close disks with parafilm and place them in the regeneration room.

Day 4. Poor plates with medium 2.

Day 5. Transfer disks to plates with medium 2 (20 disks per plate).

Day 8. Poor plates with medium 3.

Day 9. Transfer disks to plates with medium 3 (10 disks per plate). Make from the disks which are not dipped on day 3 the following controls:

1 Not dipped and NO selection (20 disks, 2 plates)

2 Not dipped and WITH selection (20 disks, 2 plates)

Make as additional control:

3 Dipped and NO selection (20 disks, 2 plates)

Transfer the disks every three weeks to fresh medium. After 3 weeks the first shoots are visible.

When the shoots are big enough, cut them of and place them in tubes with medium 4 (rooting may take 3 weeks). Sterile media needed:

Preparation of basal medium:

For 1 liter $MS_{30}R3$ 100 ml 10*MS salts 10 ml 100*R3 vitamines 30 g sucrose 8 g Diachin agar Adjust pH 5.8 with KOH and sterilize 20' 110° C.

Preparation of medium for potato stock collection:

For 1 liter 1/2 $MS_{20}R3$: 50 ml 10*MS salts 5 ml 100*MS vitamines 30 g Sucrose 8 g Daichin agar Adjust pH 5.8 with KOH and sterilize 20' 110° C.

Basal medium with proper hormones and antibiotics:

1 $MS_{30}R3+3.5$ mg/l Zeatin Riboside 500 µl stock solution (3.5 mg/ml) per 500 ml;

0.03 mg/l I.A.A. 15 µl stock solution (1.0 mg/ml) per 500 ml.

2 $MS_{30}R3+3.5$ mg/l Zeatin Riboside, 0.03 mg/l I.A.A., 200 mg/l Cefotaxime, 500 µl stock solution (200 mg/ml) per 500 ml, 100 mg/l Vancomycin 500 µl stock solution (100 mg/ml) per 500 ml 3 $MS_{30}R3+3.5$ mg/l Zeatin Riboside 0.03 mg/l I.A.A.

200 mg/l Cefotaxime 100 mg/l Vancomycin 100 mg/l Kanamycin 500 µl stock solution (100 mg/ml) per 500 ml Stock collection medium with proper hormones and antibiotics:

| | |
|---|---|
| ½ $MS_{30}R3$ + | 100 mg/l Cefotaxime |
| | 50 mg/l Vancomycin |
| | 100 mg/l Kanamycin | d. analysis of gene expression

Transgenic plants may be analysed for the Cluster-A protein on Western blots using an anti-Cluster A antiserum. If mRNA levels are tested on Northern blots a suitable cDNA fragment from Cluster-A is used as a probe. Plants with enhanced production of the cluster-A protein are tested for enhanced resistance levels against fungi. Plants which exhibit simultaneously enhanced levels of Cluster-A and β-1,3-glucanase are expected to possess a higher resistance against fungal infection.

EXPERIMENTAL

Polymerase Chain Reaction

DNA amplification was performed during 35 cycles of sequenctial incubations at 94° C. for 0.5 min, 50° C. for 2 min and 72° C. for 1.5 min, in a 50 µl reaction mixture, containing 1 ng of Cluster-A DNA, 0.2 µM of T7 primer, 0.2 µM of primer p1 and 2 units of *Thermus aguaticus* DNA polymerase (Perkin-Elmer Cetus, Gouda, The Netherlands). Part of the reaction products (4%) was electrophoresed in an agarose gel, to confirm the synthesis of a DNA fragment with the correct size. The remainder of the PCR DNA products was precipitated with ethanol and washed to remove excess of salts.

Synthesis and Analysis of cDNA Libraries

Isolation of poly(A)+-RNA from TMV-infected tobacco, the synthesis of cDNA and the construction of a cDNA library, unidirectionally cloned in the lambda vector Uni-ZAP XR, was performed according to the manufactures's instructions (Stratagene, La Jolla Calif.). Recombinant phages were screened using the $^{32}$P-labelled insert of cDNA clone PROB40 as a probe (Hooft van Huijsduijnen R. A. M. et al, 1986, EMBO J. 5, 2057–2061). After rescue of the cDNA-containing pBluescript plasmids from the isolated lambda phage by coinfection with helper phage R408 (Stratagene) the cDNA insert of Cluster-A was subcloned in M13 derivatives and sequenced using the M13 primer and a primer based on the cDNA sequence obtained with the M13 primer. Alternatively, the cDNA was directly sequenced from denatured plasmid DNA, using T3 or T7 primers (Promega, Madison Wis.; Chen & Seeburg, 1985, DNA 4, 165–170)

Protein Purification

Proteins were extracted from tobacco leaves, 7 days after infection with tobacco mosaic virus and desalted by passage through a G-25 column, equilibrated in 40 mM NaOAc, pH 5.2 (Woloshuk C. P. et al, 1991, The Plant Cell 3, 619–628). The desalted protein solution was left overnight on ice before centrifuging 50 min at 20,000 g. The resulting supernatant was loaded onto a S-Sepharose (fast flow, Pharmacia) column (5×5 cm) equilibrated in 40 mM NaOAc, pH 5.2. Adsorbed proteins were eluted with a linear salt gradient from 0 to 0.3 M NaCl in the above buffer. Every third fraction was analyzed by immunoblotting and the Cluster-A containing fractions were pooled and dialysed to 50 mM Tris, HCl pH 8.0. This solution was passed through a chelating Sepharose column (HR 10/2; Pharmacia) activated by a slightly acidic solution (50 ml) of 0.1 M $ZnCl_2$ (pH=5.4). The column was extensively washed with water (500 ml) and then equilibrated in the above Tris-buffer prior to use. The Cluster-A containing pool was loaded in several runs each containing 3 to 4 mg protein. The retarded protein peak was pooled and subjected to chelating Sepharose chromatography again. Although a tighter binding was observed after activation of the chelating sepharose column with $Cu^{2+}$-ions, purification under these conditions was less effective (data not shown). The final purification step consisted of gelfiltration through a Superdex-75 column (HR 10/30; Pharmacia equilibrated in 50 mM $KHPO_4$ buffer, pH 7.0, containing 200 mM NaCl. Gelfiltration was carried out at a flow rate of 0.5 ml per minute and fractions of 0.5 ml were collected. The fractions were analyzed by SDS-PAA gelelectrophoresis and immunoblotting.

SDS-gelelectrophoresis, Immunoblotting and Sequence Determinations

Protein samples were separated on 12.5% SDS-PAA gels as described by Laemmli (Laemmli U. K., 1970, Nature 227, 680–685). Immunoblotting and detection was performed according to the ECL Western blotting protocol provided by AMersham, UK. The antiserum to the PR-4a,b homologue from tomato (PR-P2) was kindly provided by Matthieu Joosten, Wageningen, The Netherlands. For immunodetection the antiserum to putative cluster-A protein was used in a 1:2000 dilution.

For sequencing purposes the protein was separated as described by Moos (Moos M. et al, 1988, J. Biol. Chem. 263, 6005–6008) and electroblotted onto PVDF membrane as described by Matsudaira et al. (Matsudaira et al, 1987, J. Biol. Chem. 262, 10035–10038). Proteins were visualized by Coomassie Brilliant Blue R-250 staining (Matsudaira et al, 1987, supra). Since the putative Cluster-A protein was N-terminally blocked it was acid hydrolysed on the PVDF membrane as described by Landon (Landon M., 1977, Methods of Enz. 47, 145–149). The digest (consisting of two peptides) was sequenced by Eurosequence, Groningen, The Netherlands, using Edman degradation on an Applied Biosystems 477A protein sequencer.

Enzyme Assays

Chitinase activity measurements were routinely carried out as described by Molano et al (1977, supra). Alternative assays like the blue substrate assay described by Wirth and Wolf (Wirth S. J. and Wolf G. A., 1990, J. Microbiol. Meth. 12, 197–205), the p-nitrophenyl liberation assay described by Roberts and Selitrennikoff (Roberts W. K. and Selitrennikoff C. P., 1988, J. Gen. Microbiol. 134, 169–176) and the 4-methylumbelliferone liberation assay described by McCreath and Gooday (McCreath K. J. and Gooday G. W., 1991, J. Microbiol. Meth. 14, 229–237) were also used. Lysozyme activity was determined in 50 mM $KPO_4$ buffer, pH 6.0 as described by Selsted and Martinez (1980, Anal-.Biochem. 109, 67–70).

Chitinase Assays

Bacteria induced to express the cA-3 protein and control bacteria were collected from 10 ml cultures by centrifugation and the pellets were resuspended in 1 ml TBS (20 mM Tris-HCl, pH 7.5, 150 mM NaCl). After sonification of the suspensions were stored at −20° C. Before assaying for chitinase activity, 1% Triton X-100 was added. Total protein extracts of healthy or TMV-infected tobacco leaf was obtained by homogenization in 5 ml of TBS. The homogenates were briefly centrifugated to remove the insoluble material and stored at −20° C. Extracellular proteins were obtained by vacuum infiltration of leaves with $H_2O$ (nanopure). The infiltrated leaves were placed in a syringe and centrifuged for 5 min at 3000 rpm in a table top centrifuge. The colourless washing containing the extracellular proteins was stored at −20° C. Chitin-hydrolysing activity was assayed in 200 µl reaction mixtures containing 50 µl of thouroughly washed $^3$H-labeled chitin suspension, 50 µl bacterial or plant extract and 100 µl 50 mM potassium phosphate, pH 6.4. after incubation for 30 min at 30°, 0.5 ml of 10% trichloroacetic acid was added, the mixture was centrifugated to remove precipitated material and 0.5 ml of the supernatant was removed and filtered through glasswool. Solubilized radioactivity was measured in a liquid scintilation counter.

RNA Blot and DNA Blot Analysis

Total RNA from non-stressed or stressed tobacco was extracted from frozen leaf-tissue by homogenization in extraction buffer (1 M Tris-HCl, 0.1 M LiCl, 10 mM EDTA, 1% SDS, pH 9.0). The homogenate was extracted with phenol and chloroform and the RNA was precipitated with 2 M LiCl. The RNA was electrophoresed in 1.5% agarose gels after glyoxylation and blotted to nylon membranes (Genescreen, New England Nuclear or Hybond-N, Amersham). Tobacco genomic DNA was isolated and digested, electrophoresed and blotted as described (Cornelissen et al, 1987, Nucl. Acids Res. 15, 6799–6811). Hybridization of tobacco nucleic acids was performed with the $^{32}$P-labelled cDNA insert of Cluster-A in 5× SSC, 2% SDS, 50% formamide, 100 µg/ml herring sperm DNA at 42° C. (1× SDS at 50° C. and autoradiographed.

Obtention of Agrobacterium Strain MOG101

A helper plasmid conferring the *Agrobacterium tumefaciens* virulence functions derived from the octopine Ti-plasmid pTiB6 was constructed, MOG101. MOG101 is an *Agrobacterium tumefaciens* strain carrying a non-oncogenic Ti-plasmid from which the entire T-region was substituted by a bacterial Spectinomycin resistance marker from transposon Tn 1831 (Hooykaas et al, 1980 Plasmid 4, 64–75).

The Ti-plasmid pTiB6 contains two adjacent T-regions, TL (T-left) and TR (T-right). To obtain a derivative lacking the TL- and TR-regions, we constructed intermediate vector pMOG579. Plasmid pMOG621 is a pBR322 derivative, which contains the 2 Ti-plasmid fragments that are located to the left and right, outside the T-regions (FIG. 2). In pMOG579 the 2 fragments (shown in dark) were separated by a 2.5 kb BamHI-HindIII fragment from transposon Tn1831 (Hooykaas et al, 1980 Plasmid 4, 64–75) carrying the spectinomycin resistance marker (FIG. 2). The plasmid was introduced into *Agrobacterium tumefaciens* strain LBA1010 [C58-C9 (pTiB6)=a cured C58 strain in which pTiB6 was introduced (Koekman et al (1982), Plasmid 7, 119–132) by triparental mating from *E. coli*, using HB1018 (pRK2013) as a helper. Transconjugants were selected for resistance to Rifampicin (20 mg/l) and spectinomycin (250 mg/l). A double recombination between pMOG579 and pTiB6 resulted in loss of carbenicillin resistance (the pBR322 marker) and deletion of the entire T-region. Of 5000 spectinomycin resistant transconjugants replica plated onto carbenicillin (100 mg/l) 2 were found sensitive. Southern analysis showed that a double crossing over event had deleted the entire T-region (not shown). The resulting strain was called MOG101. This strain and its construction is analogous to strain GV2260 (Deblaere et al 1985, Nucl. Acid Res. 13, 4777–4788). (MOG101 is described in more detail in Hood E., Gelvin S. B., Melchers L. S. and Hoekema A., 1993, Transgene Research 2, 208–218 and is freely available from MOGEN International N.V. upon request.

We claim:

1. A method for inhibiting growth and/or germination of a fungus by contacting the fungus or causing the fungus to be contacted with a composition comprising an effective amount of a pathogenesis-related protein occurring naturally in a plant, said protein having endochitinase activity and being encoded by the DNA sequence of SEQ ID NO: 1 or SEQ ID NO: 7 or a DNA sequence which hybridizes with a complement to SEQ ID NO: 1 or 7 under hybridization conditions including a wash at 65° C. in 0.1× SSPE, 0.1% SDS.

2. A method as claimed in claim 1, wherein said protein has a molecular weight of about 40 to 43 KDa as judged by sodium dodecyl sulphate polyacrylamide electrophoresis and wherein said protein has substantially no exochitinase activity.

3. A method as claimed in claim 1, wherein the protein has a chitinase activity on tritiated chitin as a substrate that is lower than Chi-I from tobacco by about 250 times or more and a chitinase activity on soluble chitin as a substrate that is higher than that of Chi-I from tobacco.

4. A method as claimed in claim 1, wherein the protein comprises the amino acid sequence of SEQ ID NO: 2 or SEQ ID NO: 8.

5. A method as claimed in claim 1, wherein the protein occurs naturally in leaves of TMV induced tobacco plants.

6. A method as claimed in claim 1, wherein the composition further comprises β-1,3 glucanase in an amount sufficient to enhance the effectiveness of the composition in inhibiting the growth or germination of the fungus.

7. A method as claimed in claim 6, wherein the composition further comprises another protein in an amount sufficient to enhance the effectiveness ofthe composition in inhibiting the growth or germination of the fungus.

8. A method as claimed in claim 1, wherein said pathogenesis related protein reacts with an antiserum that recognizes a protein that occurs naturally in leaves of TMV-induced tobacco plants.

9. A method as claimed in claim 1, wherein the protein is encoded by the DNA sequence of SEQ ID NO: 1 or SEQ ID NO: 7.

10. A composition for inhibiting growth and/or germination of a fungus comprising:
    a) a pathogenesis-related protein occurring naturally in a plant, said protein having endochitinase activity and being encoded by the DNA sequence of SEQ ID NO: 1 or SEQ ID NO: 7 or a DNA sequence which hybridizes with SEQ ID NOS: 1 or 7 under hybridization conditions including a wash at 65° C. in 0.1× SSPE, 0.1% SDS; and
    b) β-1,3 glucanase in an amount sufficient to enhance the effectiveness of the composition in inhibiting the growth or germination of the fungus.

11. A composition as claimed in claim 10, wherein said pathogenesis-related protein comprises the amino acid sequence of SEQ ID NO: 2 or SEQ ID NO: 8.

12. A composition as claimed in claim 11, wherein the pathogenesis-related protein has a chitinase activity on tritiated chitin as a substrate that is lower than Chi-I from tobacco by about 250 times or more and a chitinase activity on soluble chitin as a substrate that is higher than that of Chi-I from tobacco.

13. A composition as claimed in claim 10, wherein the pathogenesis-related protein reacts with an antiserum that recognizes a pathogenesis-related protein that occurs naturally in leaves of TMV-induced tobacco plants.

14. A composition as claimed in claim 10, wherein the pathogenesis-related protein occurs naturally in leaves of TMV-induced tobacco plants.

15. A composition as claimed in claim 10, wherein said composition further comprises another protein that is selected and is present in an amount sufficient to enhance the effectiveness of the composition in inhibiting the growth or germination of the fungus.

* * * * *

```
                              SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
            (A) LENGTH: 1253 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (vi) ORIGINAL SOURCE:
            (A) ORGANISM: Nicotiana tabacum
            (B) STRAIN: Samsun NN
            (D) DEVELOPMENTAL STAGE: TMV-induced (vii) IMMEDIATE SOURCE:
            (B) CLONE: Cluster-A (ix) FEATURE:
            (A) NAME/KEY: CDS
            (B) LOCATION: 14..1126
            (D) OTHER INFORMATION: /partial (xi) SEQUENCE DESCRIPTION: SEQ ID NO: 1:

CGAGTTTTTT TTT TTT TCT ATT ATT TTC TCA TGT TTC CTT CTC CGG CAA          49
                    Phe Ser Ile Ile Phe Ser Cys Phe Leu Leu Arg Gln
                     1               5                  10

CTA GTT TGC ACA AAT AGC CAA AAT GTT ATT AAG GGA GGG TAC TGG TTT         97
    Leu Val Cys Thr Asn Ser Gln Asn Val Ile Lys Gly Gly Tyr Trp Phe
                 15                  20                  25

AAG AAC AGT GGA TTA GCA TTA AAC AAC ATA GAC TCA ACA CTT TTC ACT        145
    Lys Asn Ser Gly Leu Ala Leu Asn Asn Ile Asp Ser Thr Leu Phe Thr
     30                  35                  40

CAT CTA TTT TGT GCA TTT GCT GAT CTT AAT CCA CAA TCA AAT CAG TTA        193
    His Leu Phe Cys Ala Phe Ala Asp Leu Asn Pro Gln Ser Asn Gln Leu
     45                  50                  55                  60

ATC ATT TCG CCA GAA AAT CAA GAT TCA TTC AGC CAA TTT ACA AGT ACA        241
    Ile Ile Ser Pro Glu Asn Gln Asp Ser Phe Ser Gln Phe Thr Ser Thr
                     65                  70                  75

GTT CAA AGG AAA AAT CCT TCA GTC AAG ACT TTC TTG TCT ATA GCT GGA        289
    Val Gln Arg Lys Asn Pro Ser Val Lys Thr Phe Leu Ser Ile Ala Gly
                 80                  85                  90

GGA AGA GCT GAT ACA ACT GCC TAT GGA ATT ATG GCT AGA CAA CCA AAT        337
    Gly Arg Ala Asp Thr Thr Ala Tyr Gly Ile Met Ala Arg Gln Pro Asn
             95                  100                 105

TCA AGA AAA AGT TTT ATT GAT TCA TCA ATA AGA TTG GCT AGA CAA TTT        385
    Ser Arg Lys Ser Phe Ile Asp Ser Ser Ile Arg Leu Ala Arg Gln Phe
    110                 115                 120

GGA TTT CAT GGC CTT GAT CTT GAT TGG GAA TAT CCA TTA TCA GCT ACA        433
    Gly Phe His Gly Leu Asp Leu Asp Trp Glu Tyr Pro Leu Ser Ala Thr
    125                 130                 135                 140

GAT ATG ACA AAC TTA GGG ATC CTT TTG AAT GAG TGG CGC ACC GCT ATC        481
    Asp Met Thr Asn Leu Gly Ile Leu Leu Asn Glu Trp Arg Thr Ala Ile
```

```
                  145              150              155
AAC ATG GAG GCG AGA AAT TCC GGC AGG GCG GCA CTG CTT CTC ACG GCG    529
Asn Met Glu Ala Arg Asn Ser Gly Arg Ala Ala Leu Leu Leu Thr Ala
            160              165              170

GCG GTT TCC TAC TCA CCC CGA GTC AAT GGA TTG AAC TAC CCA GTT GAA    577
Ala Val Ser Tyr Ser Pro Arg Val Asn Gly Leu Asn Tyr Pro Val Glu
            175              180              185

TCG GTG GCA AGA AAC TTA AAC TGG ATT AAC CTT ATG GCA TAT GAC TTC    625
Ser Val Ala Arg Asn Leu Asn Trp Ile Asn Leu Met Ala Tyr Asp Phe
            190              195              200

TAT GGA CCA AAT TGG TCA CCA TCA CAA ACC AAT TCA CAT GCA CAA TTA    673
Tyr Gly Pro Asn Trp Ser Pro Ser Gln Thr Asn Ser His Ala Gln Leu
205              210              215              220

TTT GAT CCT GTG AAC CAT ATT AGT GGA AGC GAT GGA ATT AAT GCA TGG    721
Phe Asp Pro Val Asn His Ile Ser Gly Ser Asp Gly Ile Asn Ala Trp
            225              230              235

ATT CAA GCT GGT GTT CCA ACA AAA AAA TTG GTA CTT GGA ATT CCA TTT    769
Ile Gln Ala Gly Val Pro Thr Lys Lys Leu Val Leu Gly Ile Pro Phe
            240              245              250

TAT GGC TAT GCG TGG CGA TTG GTT AAC CCG AAT ATC CAC GAT CTT AGA    817
Tyr Gly Tyr Ala Trp Arg Leu Val Asn Pro Asn Ile His Asp Leu Arg
            255              260              265

GCA CCT GCC GCC GGA AAA TCA AAT GTA GGT GCG GTC GAT GAT GGG TCG    865
Ala Pro Ala Ala Gly Lys Ser Asn Val Gly Ala Val Asp Asp Gly Ser
270              275              280

ATG ACT TAT AAC AGA ATT AGA GAT TAT ATA GTG CAG AGT CGC GCC ACA    913
Met Thr Tyr Asn Arg Ile Arg Asp Tyr Ile Val Gln Ser Arg Ala Thr
285              290              295              300

ACT GTG TAT AAT GCT ACT ATT GTT GGA GAT TAT TGT TAC TCT GGA AGT    961
Thr Val Tyr Asn Ala Thr Ile Val Gly Asp Tyr Cys Tyr Ser Gly Ser
            305              310              315

AAT TGG ATT AGC TAT GAT GAT ACT CAA AGT GTT AGA AAT AAG GTT AAT    1009
Asn Trp Ile Ser Tyr Asp Asp Thr Gln Ser Val Arg Asn Lys Val Asn
            320              325              330

TAT GTT AAA GGT AGA GGA TTG CTA GGT TAC TTT GCA TGG CAC GTT GCA    1057
Tyr Val Lys Gly Arg Gly Leu Leu Gly Tyr Phe Ala Trp His Val Ala
            335              340              345

GGG GAT CAA AAT TGG GGA CTT TCT CGT ACA GCT TCA CAA ACA TGG GGA    1105
Gly Asp Gln Asn Trp Gly Leu Ser Arg Thr Ala Ser Gln Thr Trp Gly
350              355              360

GTG TCA TCT CAA GAG ATG AAG TGATGGATTA CGTAATTGTG TGTGTCAAGT       1156
Val Ser Ser Gln Glu Met Lys
365              370

ATACTACTTA TAATAAGGCA ACAGATATGT GAACTATGAC ATAAATAAAT AAACAATAAA  1216

TTGTGGTCTC CAAAAAAAAA AAAAAAAAAA AAAAAAA                          1253

(2) INFORMATION FOR SEQ ID NO: 2:

(i) SEQUENCE CHARACTERISTICS:
        (A) LENGTH: 371 amino acids
        (B) TYPE: amino acid
        (D) TOPOLOGY: linear (ii) MOLECULE TYPE: protein (xi) SEQUENCE DESCRIPTION: SEQ ID NO: 2:

Phe Ser Ile Ile Phe Ser Cys Phe Leu Leu Arg Gln Leu Val Cys Thr
 1               5                  10                  15

Asn Ser Gln Asn Val Ile Lys Gly Gly Tyr Trp Phe Lys Asn Ser Gly
            20                  25                  30
```

```
Leu Ala Leu Asn Asn Ile Asp Ser Thr Leu Phe Thr His Leu Phe Cys
            35                  40                  45

Ala Phe Ala Asp Leu Asn Pro Gln Ser Asn Gln Leu Ile Ile Ser Pro
    50                  55                  60

Glu Asn Gln Asp Ser Phe Ser Gln Phe Thr Ser Thr Val Gln Arg Lys
65                  70                  75                  80

Asn Pro Ser Val Lys Thr Phe Leu Ser Ile Ala Gly Gly Arg Ala Asp
                85                  90                  95

Thr Thr Ala Tyr Gly Ile Met Ala Arg Gln Pro Asn Ser Arg Lys Ser
            100                 105                 110

Phe Ile Asp Ser Ser Ile Arg Leu Ala Arg Gln Phe Gly Phe His Gly
        115                 120                 125

Leu Asp Leu Asp Trp Glu Tyr Pro Leu Ser Ala Thr Asp Met Thr Asn
    130                 135                 140

Leu Gly Ile Leu Leu Asn Glu Trp Arg Thr Ala Ile Asn Met Glu Ala
145                 150                 155                 160

Arg Asn Ser Gly Arg Ala Ala Leu Leu Leu Thr Ala Ala Val Ser Tyr
                165                 170                 175

Ser Pro Arg Val Asn Gly Leu Asn Tyr Pro Val Glu Ser Val Ala Arg
            180                 185                 190

Asn Leu Asn Trp Ile Asn Leu Met Ala Tyr Asp Phe Tyr Gly Pro Asn
        195                 200                 205

Trp Ser Pro Ser Gln Thr Asn Ser His Ala Gln Leu Phe Asp Pro Val
    210                 215                 220

Asn His Ile Ser Gly Ser Asp Gly Ile Asn Ala Trp Ile Gln Ala Gly
225                 230                 235                 240

Val Pro Thr Lys Lys Leu Val Leu Gly Ile Pro Phe Tyr Gly Tyr Ala
                245                 250                 255

Trp Arg Leu Val Asn Pro Asn Ile His Asp Leu Arg Ala Pro Ala Ala
            260                 265                 270

Gly Lys Ser Asn Val Gly Ala Val Asp Asp Gly Ser Met Thr Tyr Asn
        275                 280                 285

Arg Ile Arg Asp Tyr Ile Val Gln Ser Arg Ala Thr Thr Val Tyr Asn
    290                 295                 300

Ala Thr Ile Val Gly Asp Tyr Cys Tyr Ser Gly Ser Asn Trp Ile Ser
305                 310                 315                 320

Tyr Asp Asp Thr Gln Ser Val Arg Asn Lys Val Asn Tyr Val Lys Gly
                325                 330                 335

Arg Gly Leu Leu Gly Tyr Phe Ala Trp His Val Ala Gly Asp Gln Asn
            340                 345                 350

Trp Gly Leu Ser Arg Thr Ala Ser Gln Thr Trp Gly Val Ser Ser Gln
        355                 360                 365

Glu Met Lys
    370

(2) INFORMATION FOR SEQ ID NO: 3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (ix) FEATURE:
```

-continued

```
        (A) NAME/KEY: misc_feature
        (B) LOCATION: 1..29
        (D) OTHER INFORMATION: /function= "pcr-primer"

(xi) SEQUENCE DESCRIPTION: SEQ ID NO: 3:

GTTTCCTTCT CCATGGAACT AGTTTGCAC                                              29

(2) INFORMATION FOR SEQ ID NO: 4:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Nicotiana tabacum
        (B) STRAIN: Samsun NN
        (D) DEVELOPMENTAL STAGE: TMV-induced
        (F) TISSUE TYPE: Leaf (ix) FEATURE:
        (A) NAME/KEY: Peptide
        (B) LOCATION: 5
        (D) OTHER INFORMATION: /label= X
              /note= "residue is Val or Ile"

(ix) FEATURE:
        (A) NAME/KEY: Peptide
        (B) LOCATION: 10
        (D) OTHER INFORMATION: /label= x
              /note= "probably Gly"

(ix) FEATURE:
        (A) NAME/KEY: Peptide
        (B) LOCATION: 14
        (D) OTHER INFORMATION: /label= x
              /note= "unknown residue"

(xi) SEQUENCE DESCRIPTION: SEQ ID NO: 4:

Pro Val Asn His Xaa Ser Gly Ser Asp Xaa Ile Asn Ala Xaa Ile Gln
1               5                   10                  15

(2) INFORMATION FOR SEQ ID NO: 5:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Nicotiana tabacum
        (D) DEVELOPMENTAL STAGE: TMV-induced
        (F) TISSUE TYPE: leaf (xi) SEQUENCE DESCRIPTION: SEQ ID NO: 5:

Gly Leu Asn Tyr Pro Val Glu Ser Val Ala Arg Asn Leu Asn Trp
1               5                   10                  15

(2) INFORMATION FOR SEQ ID NO: 6:

(i) SEQUENCE CHARACTERISTICS:
        (A) LENGTH: 26 amino acids
        (B) TYPE: amino acid
        (C) STRANDEDNESS: single
```

(D) TOPOLOGY: linear (ii) MOLECULE TYPE: peptide (iii) HYPOTHETICAL: NO (vi) ORIGINAL SOURCE:
         (A) ORGANISM: Nicotiana tabacum
         (D) DEVELOPMENTAL STAGE: TMV-induced
         (F) TISSUE TYPE: leaf (ix) FEATURE:
         (A) NAME/KEY: Peptide
         (B) LOCATION: 12
         (D) OTHER INFORMATION: /label= x
              /note= "both Val and Ile occur"

(xi) SEQUENCE DESCRIPTION: SEQ ID NO: 6:

Ser His Ala Gln Leu Phe Asp Pro Val Asn His Xaa Ser Gly Ser Asp
1               5                   10                  15

Gly Ile Asn Ala Trp Ile Gln Ala Gly Val
            20                  25

(2) INFORMATION FOR SEQ ID NO: 7:

(i) SEQUENCE CHARACTERISTICS:
         (A) LENGTH: 3155 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (vi) ORIGINAL SOURCE:
         (A) ORGANISM: Nicotiana tabacum
         (B) STRAIN: Samsun NN (ix) FEATURE:
         (A) NAME/KEY: exon
         (B) LOCATION: 454..907

(ix) FEATURE:
         (A) NAME/KEY: exon
         (B) LOCATION: 1859..2497

(ix) FEATURE:
         (A) NAME/KEY: exon
         (B) LOCATION: 2847..2884

(ix) FEATURE:
         (A) NAME/KEY: intron
         (B) LOCATION: 908..1858

(ix) FEATURE:
         (A) NAME/KEY: intron
         (B) LOCATION: 2498..2846

(ix) FEATURE:
         (A) NAME/KEY: CDS
         (B) LOCATION: join(454..907, 1859..2497, 2847..2884)

(xi) SEQUENCE DESCRIPTION: SEQ ID NO: 7:

GAGCTCTGTT AATAATTTTG ACGTAACTAG TCATCAGGTC GCAGTTCAAG TCATCAGGTA      60

GCAGTTCAAG TCATGAAAAT AGTCTCTTGC AGGTAAGGTT GCGTACAACA GATCCTTGTG     120

GTCCGGCCCT TTCCGAACTT CGCTTGTAGC TGGAGCTTAG TCACCGGAAT ACCCGTTGTT     180

CCGTTAATAA CAAGAACACA TACAAGACGA TTTGCTAACA AAATATATA TATAAACCAA      240

AAGTGTAACG ATGATAAAAT TGCACAATTC TGAAGGATAT ACAGGAAAAT TTTGACCTTT     300

TCTCTATTTA GAAATATTGA GAGATTCAAC CACTTTCTAA TGGAGTAGTA AATGTATCGC     360

| | |
|---|---|
| AAACTAAAAG CCGCCGGTAG ACAGTAAACT CAAATCTTCA AACTTATTTA AACTCGAAGT | 420 |

```
CACAAATTAA ATAAGCTATC AACCTTCAAT TTA ATG GCT AAT TCT GTC ACT CTT      474
                                    Met Ala Asn Ser Val Thr Leu
                                      1               5

TTC GCC ATT ATT TTC TCA TGT TTC CTC CTC CAG CAA CTA GTT TGC ACA      522
Phe Ala Ile Ile Phe Ser Cys Phe Leu Leu Gln Gln Leu Val Cys Thr
         10              15                  20

AAT AGC CAA AAT GTT AAG GGA GGA TAC TGG TTT AAG GAC AGT GGA TTA      570
Asn Ser Gln Asn Val Lys Gly Gly Tyr Trp Phe Lys Asp Ser Gly Leu
         25              30              35

GCA TTA AAC AAC ATA GAT TCA ACA CTT TTC ACT CAT CTA TTT TGT GCA      618
Ala Leu Asn Asn Ile Asp Ser Thr Leu Phe Thr His Leu Phe Cys Ala
 40              45              50              55

TTT GCC GAT CTT AAT CCT CAA TTA AAT CAG TTA ATT ATT TCG CCG GAA      666
Phe Ala Asp Leu Asn Pro Gln Leu Asn Gln Leu Ile Ile Ser Pro Glu
             60              65              70

AAT CAA GAT TCA TTC AGG CAA TTT ACA AGT ACA GTT CAA AGG AAA AAT      714
Asn Gln Asp Ser Phe Arg Gln Phe Thr Ser Thr Val Gln Arg Lys Asn
             75              80              85

CCT TCG GTC AAG ACT TTC TTG TCT ATA GCT GGA GGA AGA GCT AAT TCA      762
Pro Ser Val Lys Thr Phe Leu Ser Ile Ala Gly Gly Arg Ala Asn Ser
         90              95              100

ACT GCC TAT GGA ATT ATG GCT AGA CAA CCA AAT TCA AGA AAA AGT TTT      810
Thr Ala Tyr Gly Ile Met Ala Arg Gln Pro Asn Ser Arg Lys Ser Phe
 105             110             115

ATT GAT TCA TCA ATA AGA TTG GCT AGA CAA TTA GGA TTT CAT GGC CTT      858
Ile Asp Ser Ser Ile Arg Leu Ala Arg Gln Leu Gly Phe His Gly Leu
 120             125             130             135

GAT CTT GAT TGG GAA TAT CCA TTA TCA GCT GCA GAC ATG ACA AAC TTA G    907
Asp Leu Asp Trp Glu Tyr Pro Leu Ser Ala Ala Asp Met Thr Asn Leu
             140             145             150
```

| | |
|---|---|
| GTATTATTGA CAAACATATA TTTTCTTCAT TTGTTTTACA CATATGGATG CCCCTTACAT | 967 |
| GAATTTATTT TTGGACAAAT ATAGCTAGTT GTGAATTTAG GAGAGGCAAT CGGGCGGGTC | 1027 |
| GTGTCGGATA TGGGATGGAT TGAAAATGGA TAATGAAAAA ATGGATAAAG TATCCGACCC | 1087 |
| GATTCATATT TAATACGGAT AATAAACCGG TCCATGACTT CTTGAATATG ATCCCTTTTG | 1147 |
| GGAGAATTTC TATTTTCCCA AACTTACCCC CAATTTGAAG CTTTATAAAT GCAAAAGTTA | 1207 |
| AACTCATTAG TTATCCATTG ATTATCCATT TTCCAAATGG ATAATATGAT TCTTATTTAT | 1267 |
| ATTTGACCCG TTTTTAAAAA GTTCATTATC CAACCCATTT TTAGTGGATA ATATGGGTGG | 1327 |
| TTAATTCTTT TCTTTTAACC ATTTTGCCAT CACTAGTTGT GATATTTGAA CTCTCATCTG | 1387 |
| TCTGTTCAGA TATTATATTG AATTATGTGA CAACAGTATT TGAAATTAGA AATTATTATA | 1447 |
| CACATAATAT ATTTTTATTT ACTTAATTAT CATATCTCTG ACTGCAATAC TAGGTTCTTG | 1507 |
| ATACTAGACA CATTATATGT AACTTTTGCA AATTATGGGT CTATGATATT TTCGAAAATA | 1567 |
| ATAACAATTT TTTCACTCTC CTCACAGTTA TATATAATCT CGAAAGGGGA AAGATCCCTC | 1627 |
| AGAGAATCAC TCGATTATAT TGACAAGTTC AAAAAACTGA TCATAATATG ATGGCGATTG | 1687 |
| CAAGCAGGCC CCCATCATCT CATAACAACT GATAGGTTTC GTTAAACCTG CTCATTATAT | 1747 |
| CCATATGTCT ACTATGATAC CATACAATAT GAATTGTGTA ATCACTCCAT CTAGCTAACA | 1807 |
| ATTTAAACTG TTGAAGAGTA CACTTTTATT TACTTACCTG TTAATTAAAC A  GG ACC | 1863 |

```
                                                         Gly Thr

CTT TTG AAT GAG TGG CGC ACC GCT ATC AAC ACG GAG GCG AGA AAT TCC     1911
Leu Leu Asn Glu Trp Arg Thr Ala Ile Asn Thr Glu Ala Arg Asn Ser
         155             160             165

GGT AGG GCG GCA CTA CTT CTC ACG GCG GCG GTT TCC AAC TCA CCC CGA     1959
```

```
Gly Arg Ala Ala Leu Leu Leu Thr Ala Ala Val Ser Asn Ser Pro Arg
170                 175                 180                 185

GTC AAT GGG TTG AAC TAC CCA GTT GAA TCA TTG GCA AGA AAC TTA GAC           2007
Val Asn Gly Leu Asn Tyr Pro Val Glu Ser Leu Ala Arg Asn Leu Asp
                190                 195                 200

TGG ATT AAC CTT ATG GCC TAT GAT TTC TAT GGA CCA AAT TGG TCA CCA           2055
Trp Ile Asn Leu Met Ala Tyr Asp Phe Tyr Gly Pro Asn Trp Ser Pro
            205                 210                 215

TCA CAA ACC AAT TCA CAT GCA CAA TTA TTT GAT CCT GTG AAC CAT GTT           2103
Ser Gln Thr Asn Ser His Ala Gln Leu Phe Asp Pro Val Asn His Val
        220                 225                 230

AGT GGA AGT GAT GGA ATT AAT GCA TGG ATT CAA GCT GGT GTT CCA ACA           2151
Ser Gly Ser Asp Gly Ile Asn Ala Trp Ile Gln Ala Gly Val Pro Thr
    235                 240                 245

AAA AAA TTG GTG CTT GGA ATT CCA TTT TAT GGC TAT GCG TGG CGA TTA           2199
Lys Lys Leu Val Leu Gly Ile Pro Phe Tyr Gly Tyr Ala Trp Arg Leu
250                 255                 260                 265

GTT AAC GCG AAT ATT CAC GGT CTT AGA GCA CCT GCT GCC GGA AAA TCA           2247
Val Asn Ala Asn Ile His Gly Leu Arg Ala Pro Ala Ala Gly Lys Ser
                270                 275                 280

AAT GTT GGT GCG GTC GAT GAT GGG TCG ATG ACT TAT AAC AGA ATT AGG           2295
Asn Val Gly Ala Val Asp Asp Gly Ser Met Thr Tyr Asn Arg Ile Arg
            285                 290                 295

GAT TAT ATA GTG GAG AGT CGC GCC ACG ACT GTG TAT AAC GCT ACC ATT           2343
Asp Tyr Ile Val Glu Ser Arg Ala Thr Thr Val Tyr Asn Ala Thr Ile
        300                 305                 310

GTT GGA GAT TAT TGT TAC TCT GGT AGT AAT TGG ATT AGC TAT GAT GAT           2391
Val Gly Asp Tyr Cys Tyr Ser Gly Ser Asn Trp Ile Ser Tyr Asp Asp
    315                 320                 325

ACT CAA ACT GTT AGA AAT AAG GTT AAT TAT GTT AAA GGT AGA GGA TTG           2439
Thr Gln Thr Val Arg Asn Lys Val Asn Tyr Val Lys Gly Arg Gly Leu
330                 335                 340                 345

CTT GGT TAT TTT GCA TGG CAC GTT GCA GGG GAT CAA AAT TGG GGA CTT           2487
Leu Gly Tyr Phe Ala Trp His Val Ala Gly Asp Gln Asn Trp Gly Leu
                350                 355                 360

TCT CGT ACA  G GTTAGACGTA GTTTTTCTTT GTTTTTTTTT TTAATTCTGG                2537
Ser Arg Thr

TATTTATATT TTTGTATGGA TAACACGTAA TTTTGTCGAA TACATAATTG TCAAAATACA         2597

TCATTTTTAT TGGTGCATGT TTTCTCATGA ATTCTTAGGA AAGCATGACT ATGCTATTTG         2657

GTCGATAGTC TTGTGAAATT TTATACATAA TCAATGCTTT TAAGGTCGGA ATTATTAGAC         2717

AATTGTCTTT CTCAATTAAT TATTATTATT ATTATTATTA TTATTATTAT TATTATTATT         2777

ATTATTATTA TTATTATTAT TATTATTATT ATTATTATTA TTTACATTTC CCCCACTTGT         2837

GTCTTGCAG  CT TCA CAA ACA TGG GGA GTG TCA TTT CAA GAG ATG AAG             2884
           Ala Ser Gln Thr Trp Gly Val Ser Phe Gln Glu Met Lys
               365                 370                 375

TGATGGATTA CGTAATTGTG TTTGTCAAGT ATCCTACTTA TAATAAGGTG ACAGATATGT         2944

GAACTATGAC ATAAATAAAA TAAATATAAA TCGGGTTCCC CAATTTTATT TTTCTACGAA         3004

TAATATATTT CTTCCCCCTT TGGAGTACAT TAGGTTTATT ATTGTTATTA TTGTTGTTGT         3064

TGTTGTTTGT ACTAATAATA TATTTCTTCG TTCCAAAATA GTTGATGCTT TTTGTTTTTC         3124

GATATTATTT TCTCGTTTTC AATTAATTAA A                                        3155

(2) INFORMATION FOR SEQ ID NO: 8:

(i) SEQUENCE CHARACTERISTICS:
        (A) LENGTH: 377 amino acids
        (B) TYPE: amino acid
```

(D) TOPOLOGY: linear (ii) MOLECULE TYPE: protein (xi) SEQUENCE DESCRIPTION: SEQ ID NO: 8:

Met Ala Asn Ser Val Thr Leu Phe Ala Ile Ile Phe Ser Cys Phe Leu
 1               5                   10                  15

Leu Gln Gln Leu Val Cys Thr Asn Ser Gln Asn Val Lys Gly Gly Tyr
                20                  25                  30

Trp Phe Lys Asp Ser Gly Leu Ala Leu Asn Asn Ile Asp Ser Thr Leu
            35                  40                  45

Phe Thr His Leu Phe Cys Ala Phe Ala Asp Leu Asn Pro Gln Leu Asn
        50                  55                  60

Gln Leu Ile Ile Ser Pro Glu Asn Gln Asp Ser Phe Arg Gln Phe Thr
 65                 70                  75                  80

Ser Thr Val Gln Arg Lys Asn Pro Ser Val Lys Thr Phe Leu Ser Ile
                85                  90                  95

Ala Gly Gly Arg Ala Asn Ser Thr Ala Tyr Gly Ile Met Ala Arg Gln
                100                 105                 110

Pro Asn Ser Arg Lys Ser Phe Ile Asp Ser Ser Ile Arg Leu Ala Arg
                115                 120                 125

Gln Leu Gly Phe His Gly Leu Asp Leu Asp Trp Glu Tyr Pro Leu Ser
        130                 135                 140

Ala Ala Asp Met Thr Asn Leu Gly Thr Leu Leu Asn Glu Trp Arg Thr
145                 150                 155                 160

Ala Ile Asn Thr Glu Ala Arg Asn Ser Gly Arg Ala Ala Leu Leu Leu
                165                 170                 175

Thr Ala Ala Val Ser Asn Ser Pro Arg Val Asn Gly Leu Asn Tyr Pro
            180                 185                 190

Val Glu Ser Leu Ala Arg Asn Leu Asp Trp Ile Asn Leu Met Ala Tyr
        195                 200                 205

Asp Phe Tyr Gly Pro Asn Trp Ser Pro Ser Gln Thr Asn Ser His Ala
    210                 215                 220

Gln Leu Phe Asp Pro Val Asn His Val Ser Gly Ser Asp Gly Ile Asn
225                 230                 235                 240

Ala Trp Ile Gln Ala Gly Val Pro Thr Lys Lys Leu Val Leu Gly Ile
                245                 250                 255

Pro Phe Tyr Gly Tyr Ala Trp Arg Leu Val Asn Ala Asn Ile His Gly
            260                 265                 270

Leu Arg Ala Pro Ala Ala Gly Lys Ser Asn Val Gly Ala Val Asp Asp
        275                 280                 285

Gly Ser Met Thr Tyr Asn Arg Ile Arg Asp Tyr Ile Val Glu Ser Arg
    290                 295                 300

Ala Thr Thr Val Tyr Asn Ala Thr Ile Val Gly Asp Tyr Cys Tyr Ser
305                 310                 315                 320

Gly Ser Asn Trp Ile Ser Tyr Asp Asp Thr Gln Thr Val Arg Asn Lys
                325                 330                 335

Val Asn Tyr Val Lys Gly Arg Gly Leu Leu Gly Tyr Phe Ala Trp His
            340                 345                 350

Val Ala Gly Asp Gln Asn Trp Gly Leu Ser Arg Thr Ala Ser Gln Thr
        355                 360                 365

Trp Gly Val Ser Phe Gln Glu Met Lys
    370                 375

(2) INFORMATION FOR SEQ ID NO: 9:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: cDNA (iii) HYPOTHETICAL: YES (xi) SEQUENCE DESCRIPTION: SEQ ID NO: 9:

AATACGACTC ACTATAG                                                17

(2) INFORMATION FOR SEQ ID NO: 10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 10:

TCTCCGGCAA CTAGTTTGCA C                                           21

(2) INFORMATION FOR SEQ ID NO: 11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 11:

GTCATAGTTC ACATATCTGT TGCC                                        24

(2) INFORMATION FOR SEQ ID NO: 12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 12:

TTTAAACTCG AAGTCACAAA TTAAA                                       25

(2) INFORMATION FOR SEQ ID NO: 13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 13:

```
TTTAAACTCG GATCCACAAA TTAAA                                          25

(2) INFORMATION FOR SEQ ID NO: 14:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 14:

AATTGTCTAG AC                                                        12
```